US011805799B2

(12) United States Patent
Chung

(10) Patent No.: US 11,805,799 B2
(45) Date of Patent: Nov. 7, 2023

(54) COMPOSITION FOR PREVENTING, RELIEVING OR TREATING CLIMACTERIC DISORDERS COMPRISING LACTIC ACID BACTERIA AND PREBIOTICS

(71) Applicant: CELL BIOTECH CO., LTD., Gyeonggi-do (KR)

(72) Inventor: Myung Jun Chung, Seoul (KR)

(73) Assignee: CELL BIOTECH CO., LTD., Gyeonggi-Do (KR)

( * ) Notice: Subject to any disclaimer, the term of this patent is extended or adjusted under 35 U.S.C. 154(b) by 152 days.

(21) Appl. No.: 16/952,635

(22) Filed: Nov. 19, 2020

(65) Prior Publication Data
US 2021/0204583 A1 Jul. 8, 2021

(30) Foreign Application Priority Data
Nov. 25, 2019 (KR) .................. 10-2019-0152441

(51) Int. Cl.
*A23L 33/135* (2016.01)
*A61P 15/00* (2006.01)
*A61K 35/745* (2015.01)
*A61K 35/747* (2015.01)

(52) U.S. Cl.
CPC .......... *A23L 33/135* (2016.08); *A61K 35/745* (2013.01); *A61K 35/747* (2013.01); *A61P 15/00* (2018.01); *A23Y 2220/37* (2013.01); *A23Y 2220/39* (2013.01); *A23Y 2220/73* (2013.01); *A23Y 2300/29* (2013.01); *A23Y 2300/45* (2013.01); *A23Y 2300/49* (2013.01); *A23Y 2300/55* (2013.01)

(58) Field of Classification Search
CPC ........ A23L 33/135; A23L 33/11; A23L 33/30; A23L 33/105; A23L 11/07; A61K 35/745; A61K 35/747; A61K 31/352; A61K 35/744; A61K 36/48; A61K 45/06; A61K 2300/00; A61P 15/00; A61P 5/24; A61P 5/30; A61P 15/12; A61P 19/10; A61P 3/06; A61P 9/06; A61P 17/14; A61P 25/20; A61P 25/24; A23Y 2220/37; A23Y 2220/39; A23Y 2220/73; A23Y 2300/29; A23Y 2300/45; A23Y 2300/49; A23Y 2300/55; A23Y 2240/41; A23V 2002/00; A23V 2200/30; A23V 2250/2116; A23V 2250/21
See application file for complete search history.

(56) References Cited

U.S. PATENT DOCUMENTS

| 7,025,998 | B2 * | 4/2006 | Senin | A61K 36/11 |
| | | | | 424/93.1 |
| 10,111,856 | B2 * | 10/2018 | Shin | A61P 29/00 |
| 2011/0236358 | A1 * | 9/2011 | Sala | A61P 5/00 |
| | | | | 424/93.4 |

FOREIGN PATENT DOCUMENTS

| KR | 1020100121566 | | 11/2010 | |
| KR | 1020110102445 | | 9/2011 | |
| KR | 20130083692 A | * | 7/2013 | ............ A23C 11/10 |
| KR | 20130083692 A | | 7/2013 | |
| KR | 20140131881 A | | 11/2014 | |
| KR | 20150007851 A | | 1/2015 | |
| KR | 20170046829 A | | 5/2017 | |
| KR | 20190014056 A | | 2/2019 | |
| WO | 2010/032838 A1 | | 3/2010 | |

OTHER PUBLICATIONS

Ali et al., of soybean isoflavones, probiotics, and their interactions on lipid metabolism and endocrine system in an animal model of obesity and diabetes, Journal of Nutritional Biochemistry 15 (2004) 583-590 (Year: 2004).*
Imhof et al., Soy germ extract alleviates menopausal hot flushes: placebo controlled double-blind trial, European Journal of Clinical Nutrition (2018) 72:961-970. (Year: 2018).*
Office Action issued in corresponding Chinese Patent Application No. 202011325147.X dated Jun. 8, 2022.
Korean Office Action dated Jul. 27, 2021; 5 Pgs.

* cited by examiner

*Primary Examiner* — Renee Claytor
*Assistant Examiner* — Tiffany M Gough
(74) *Attorney, Agent, or Firm* — Tarolli, Sundheim, Covell & Tummino, L.L.P.

(57) ABSTRACT

The present disclosure relates to a composition for preventing, relieving or treating climacteric symptoms, the composition comprising lactic acid bacteria and prebiotic composition. The lactic acid bacteria of the present disclosure have β-glucosidase activity and a very excellent ability to convert isoflavones into equol compounds, and thus may exhibit estrogenic activity through synergism with the gut microbiota. Therefore, the lactic acid bacteria of the present disclosure may be effectively used for the prevention, relief or treatment of women's climacteric or menopausal symptoms.

4 Claims, 23 Drawing Sheets

Specification includes a Sequence Listing.

Figure 7b

| Parameters | Sham | OVX | OVX + E2 | OVX + Probiotics | OVX + S30 | OVX + S30 + Probiotics |
|---|---|---|---|---|---|---|
| Albumin (g/dL) | 3.64 ± 0.12 | 2.35 ± 0.18 ᵇ | 3.44 ± 0.08 ᵈ | 2.73 ± 0.11 ᵇ,ᵈ,ᶠ | 2.46 ± 0.05 ᵇ,ᵈ | 2.88 ± 0.11 ᵇ,ᵈ,ᶠ |
| Calcium (mg/dL) | 11.05 ± 0.29 | 13.00 ± 0.47 ᵇ | 10.96 ± 0.29 ᵈ | 9.88 ± 0.35 ᵇ,ᵈ | 9.93 ± 0.30 ᵇ,ᵈ,ᶠ | 9.25 ± 0.13 ᵇ,ᵈ,ᶠ |
| Cholesterol (mg/dL) | 97.50 ± 7.66 | 138.50 ± 7.15 ᵇ | 114.33 ± 11.34 ᵃ,ᵈ | 104.33 ± 8.64 ᵈ | 121.17 ± 8.42 ᵇ,ᶜ,ᵈ | 94.00 ± 8.94 ᵈ,ᶠ |
| Triglycerides (mg/dL) | 53.83 ± 17.40 | 199.00 ± 17.68 ᵇ | 76.25 ± 8.60 ᵈ | 60.00 ± 18.55 ᵈ | 115.25 ± 17.21 ᵇ,ᶜ,ᵈ,ᵉ | 55.00 ± 7.70 ᵈ |
| HDL (mg/dL) | 61.45 ± 3.89 | 40.33 ± 5.34 ᵇ | 56.72 ± 3.52 ᵈ | 59.33 ± 4.00 ᵈ | 51.35 ± 3.65 ᵇ,ᵈ | 67.48 ± 5.08 ᵇ,ᵈ,ᶠ |
| LDL (mg/dL) | 39.84 ± 5.28 | 77.89 ± 7.57 ᵇ | 47.21 ± 4.94 ᵈ | 40.94 ± 5.02 ᵈ | 59.91 ± 5.69 ᵇ,ᶜ,ᵈ | 26.30 ± 4.32 ᵇ,ᵈ,ᶠ |
| AST (IU/L) | 82.97 ± 19.08 | 159.43 ± 26.69 ᵇ | 112.28 ± 6.60 ᶜ | 105.93 ± 15.76 ᵈ | 163.90 ± 19.01 ᵇ,ᵉ | 78.89 ± 8.10 ᵈ,ᶠ |
| ALT (IU/L) | 34.64 ± 4.23 | 63.30 ± 6.92 ᵇ | 28.70 ± 3.71 ᵈ | 40.45 ± 7.50 ᵈ,ᵉ | 57.65 ± 5.44 ᵇ,ᶜ,ᵉ | 29.40 ± 2.59 ᵈ |

Figure 9c

| Parameters | Sham | OVX | OVX + E2 | OVX + Probiotics | OVX + S30 | OVX + S30 + Probiotics |
|---|---|---|---|---|---|---|
| BMD (mgHA/ccm) | 421.250 ± 53.920 | 72.700 ± 11.193 b | 161.454 ± 37.643 b,d | 108.621 ± 16.462 b,d | 99.203 ± 11.652 b,d | 133.690 ± 21.226 b,d,e |
| TV (mm³) | 9.395 ± 1.161 | 9.885 ± 1.041 | 9.374 ± 1.031 | 9.980 ± 1.783 | 9.312 ± 0.473 | 9.950 ± 1.204 |
| BV (mm³) | 4.334 ± 0.983 | 0.637 ± 0.140 b | 1.447 ± 0.430 b,d | 0.957 ± 0.353 b,c | 0.782 ± 0.029 b,c | 1.221 ± 0.332 b,d,e |
| BV/TV (%) | 46.092 ± 8.705 | 6.410 ± 1.060 b | 15.383 ± 4.325 b,d | 9.238 ± 1.916 b,c | 8.415 ± 0.399 b,c | 12.243 ± 1.553 b,d,e |
| BS (mm²) | 69.439 ± 8.148 | 16.390 ± 3.133 b | 30.656 ± 9.187 b,d | 23.773 ± 8.996 b,d | 18.910 ± 2.316 b,c | 28.280 ± 6.413 b,d,e |
| BS/BV (1/mm) | 17.257 ± 3.198 | 32.718 ± 2.730 b | 24.431 ± 1.870 b,d | 31.768 ± 1.697 b,d | 29.654 ± 3.992 b | 26.991 ± 1.321 b,d |
| Tb. Th (mm) | 0.124 ± 0.016 | 0.079 ± 0.005 b | 0.096 ± 0.005 b,d | 0.079 ± 0.004 b,c | 0.086 ± 0.010 b | 0.093 ± 0.005 b,d |
| Tb. N (1/mm) | 5.209 ± 0.286 | 3.181 ± 0.238 b | 3.489 ± 0.492 b | 3.473 ± 0.333 b | 3.259 ± 0.247 b | 3.556 ± 0.462 b |
| Tb. Sp (mm) | 0.189 ± 0.019 | 0.332 ± 0.024 b | 0.302 ± 0.046 b | 0.314 ± 0.034 b | 0.332 ± 0.029 b | 0.286 ± 0.039 b |

COMPOSITION FOR PREVENTING, RELIEVING OR TREATING CLIMACTERIC DISORDERS COMPRISING LACTIC ACID BACTERIA AND PREBIOTICS

CROSS-REFERENCE TO RELATED APPLICATION(S)

This application claims priority to Korean Patent Application No. 10-2019-0152441, filed on Nov. 25, 2019, the disclosure of which is incorporated herein by reference in its entirety.

BACKGROUND

Technical Field

The present disclosure relates to a composition for preventing, relieving or treating climacteric symptoms comprising lactic acid bacteria and prebiotics.

Description of the Related Art

Women's menopause is the cessation of menstruation resulting from loss of genetically predetermined ovarian function at about 50 years of age. It means loss of reproductive capacity, and is not a pathological phenomenon, but is a physiological change. Currently, the average life expectancy of Korean women is 81.2 years (2011, Statistics Korea). Assuming that the average menopausal age of Korean women prescribed by the Korean Association of Obstetricians and Gynecologists is 50 years, this assumption means that women live about one-third or more of their lives depleted of female hormones. The women's climacteric period is a transitional period in which women reproductive capacity is reduced and disappears before and after menopause and in which women are physically and mentally very unstable. The climacteric period usually refers to a period ranging from 3 to 5 years before menopause through about 10 years after menopause, and corresponds to about 46 to 55 years old. In addition, menopause is defined as the time after menstruation stops completely for one year. In this regard, women undergo physical and mental changes, which vary between the premenopausal period, the menopausal transition period, the menopausal period, and the postmenopausal period.

In recent years, since several negative studies on hormone therapy were reported, the effectiveness of hormone therapy has faced many challenges. A representative of them is the WHI study published in 2002 with the support of the National Institute of Health (NIH). This study was conducted from 1993 on how hormone therapy affects primary coronary artery disease, breast cancer, rectal cancer, and secondary fractures. The WHI study was planned to proceed for 8.5 years, but was stopped early, because it was found that, after 5.2 years of administration, the risk of breast cancer significantly increased in the hormone-treated group and the incidence of cardiovascular disease significantly increased in the hormone-treated group.

Phytoestrogens are substances present in plants, and refer to substances that are structurally and functionally associated with 17-β-estradiol or exhibit estrogen effects. Phytoestrogens are roughly classified into four types as follows: (i) steroids such as pomegranate, jujube or coconut palm steroids; (ii) saponin-containing substances such as red *ginseng*; (iii) phenols such as flavonoids; and (iv) terpenoids such as *Cimicifuga heracleifolia* or licorices. Among them, flavonoids are classified into isoflavones such as soybean and red clover isoflavones, lignans such as linseed and blueberry lignans, and coumestans such as sunflower seed oil and red clover coumestans.

Isoflavones derived from soy are mostly in the form of glycoside conjugates (daidzin, genistin, and glycitin), which have low bioavailability and estrogenic activity. In order to increase the uptake and activation thereof, isoflavone aglycones (daidzein, genistein, and glycitein) which are degradation products of glycosides are required, which are produced by β-glycosidase from the intestinal microbiota (gut microbiota). In addition, these isoflavone aglycones are finally converted into equol by the gut microbiota to make up the form of phytoestrogens. The amount of equol produced by the gut microbiota is different between Asians and Westerners. About 50% of Asians who usually eat soy make equol by eating soy, but only 20 to 30% of Westerners who eat relatively little soy can make equol.

Equol exhibits the highest estrogenic activity among isoflavones. Equol and estrogen have very similar molecular structures. Equol binds to estrogen receptors (ERα and ERβ) and exhibits an activity expressed by estrogen. In particular, equol exhibits high affinity for ERβ. Although daidzein also exhibits estrogen receptor (ER) binding affinity, equol exhibits higher ER binding affinity than daidzein.

The patent documents and references mentioned herein are incorporated herein by reference to the same extent as if each reference is individually and clearly specified by reference.

PRIOR ART DOCUMENTS

Patent Documents (Patent Document 1) Korean Patent Application Publication No. 2019-0014056
(Patent Document 2) Korean Patent Application Publication No. 2014-0131881
(Patent Document 3) Korean Patent Application Publication No. 2015-0007851

SUMMARY

The present inventors have conducted studies and made efforts to develop a probiotic lactic acid bacteria strain that may be used for the prevention, relief and treatment of women's climacteric or menopausal symptoms. As a result, the present inventors have developed lactic acid bacteria, which have high β-glycosidase activity and can convert isoflavones into equol compounds with high efficiency, and have experimentally demonstrated and found that the lactic acid bacteria exhibit estrogenic activity in cell experiments and menopausal animal models, thereby completing the present disclosure.

Therefore, an object of the present disclosure is to provide a food composition for preventing or alleviating climacteric or menopausal symptoms, the food composition comprising: lactic acid bacteria; and a prebiotic composition comprising isoflavone.

Another object of the present disclosure is to provide a pharmaceutical composition for preventing or treating climacteric or menopausal symptoms, the pharmaceutical composition comprising: lactic acid bacteria; and a prebiotic composition comprising isoflavone.

Other objects and technical features of the present disclosure will be illustrated in more detail by the following detailed description, the appended claims and the accompanying drawings.

According to one aspect of the present disclosure, the present disclosure provides a food composition for preventing or alleviating climacteric or menopausal symptoms, the food composition comprising: (i) one or more lactic acid bacteria selected from the group consisting of lactic acid bacteria of the genus *Bifidobacterium*, lactic acid bacteria of the genus *Lactobacillus*, and lactic acid bacteria of the genus *Lactococcus*; and (ii) a prebiotic composition comprising isoflavone and a soybean germ extract.

The lactic acid bacteria of the present disclosure may be probiotic lactic acid bacteria in the sense that when they are administered in vivo, they settle in the gut and have a beneficial synergistic effect with the gut microbiota.

The lactic acid bacteria that are used in the present disclosure are one or more lactic acid bacteria selected from the group consisting of lactic acid bacteria of the genus *Bifidobacterium*, lactic acid bacteria of the genus *Lactobacillus*, and lactic acid bacteria of the genus *Lactococcus*.

In one embodiment of the present disclosure, the lactic acid bacteria of the genus *Bifidobacterium* are one or more lactic acid bacteria selected from the group consisting of *Bifidobacterium lactis*, *Bifidobacterium breve*, *Bifidobacterium longum*, and *Bifidobacterium infantis*.

In another embodiment of the present disclosure, the lactic acid bacteria of the genus *Lactobacillus* are one or more lactic acid bacteria selected from the group consisting of *Lactobacillus rhamnosus*, *Lactobacillus gasseri*, and *Lactobacillus helveticus*.

In still another embodiment of the present disclosure, the lactic acid bacteria of the genus *Lactococcus* are *Lactococcus lactis*.

In yet another embodiment of the present disclosure, the lactic acid bacteria may be one or more lactic acid bacteria selected from the group consisting of *Bifidobacterium lactis*, *Bifidobacterium infantis*, *Lactobacillus gasseri*, and *Lactobacillus helveticus*.

In still yet another embodiment of the present disclosure, the lactic acid bacteria may be a combination of two or more lactic acid bacteria selected from the group consisting of *Bifidobacterium lactis*, *Bifidobacterium infantis*, *Lactobacillus gasseri*, and *Lactobacillus helveticus*.

In a further embodiment of the present disclosure, the lactic acid bacteria may be a combination of four lactic acid bacteria selected from the group consisting of *Bifidobacterium lactis*, *Bifidobacterium infantis*, *Lactobacillus gasseri*, and *Lactobacillus helveticus*.

The food composition of the present disclosure comprises a prebiotic composition comprising isoflavone and a soybean germ extract.

As used herein, the term "prebiotics" refers to compounds that act as a substrate for the above-described lactic acid bacteria of the present disclosure and promote the growth or useful activity of the lactic acid bacteria.

In the present disclosure, the prebiotic component promotes the growth of the lactic acid bacteria of the present disclosure, and is converted into an equol compound by the lactic acid bacteria of the present disclosure.

In one embodiment of the present disclosure, the isoflavone may be comprised in an amount of 1 to 50 wt %, preferably 5 to 45 wt %, more preferably 10 to 40 wt %, based on the weight of the prebiotic composition.

The lactic acid bacteria of the present disclosure exhibit a very high β-glucosidase activity.

As used herein, the term "climacteric symptoms" or "menopausal symptoms" refers to symptoms appearing during the menopausal period in which the production and activity of female hormones decreases due to the gradual loss of ovarian function in women. Female hormones whose activity and production decreases during the climacteric period may include, for example, estrogen. The estrogen is a generic term for hormones such as estrone, estradiol, and estriol, and among them, estradiol is the most powerful female hormone.

In the present disclosure, the climacteric or menopausal symptoms may be, for example, but not limited to, hot flashes, night sweat, irregular menstrual cycles, loss of sexual desire, vaginal dryness, fatigue, hair loss, sleep disorder, attention difficulties, memory loss, dizziness, weight gain, incontinence, abdominal bloating, allergies, brittle nails, changes in body odor, irregular heartbeats, depression, anxiety, restlessness, panic disorder symptoms, osteoporosis, osteopenia, hyperlipidemia, or dyslipidemia.

The food composition of the present disclosure may be prepared as a functional food, a nutritional supplement, a health food or a food additive, but is not limited thereto.

The food composition of the present disclosure may be prepared in various forms according to conventional methods known in the art. For example, it may be prepared in the form of beverages such as fermented milk or in the form of powder.

The food composition of the present disclosure may comprise, in addition to the above-described active ingredient of the present disclosure, components that are generally added in the preparation of food. For example, it comprises proteins, carbohydrates, fats, nutrients, seasonings, and flavoring agents. Examples of the carbohydrate include conventional sugars such as monosaccharides, for example, glucose, fructose, etc.; disaccharides, for example, maltose, sucrose, oligosaccharide, etc.; polysaccharides, for example, dextrin, cyclodextrin, etc.; and sugar alcohols such as xylitol, sorbitol, erythritol, etc. Examples of the flavoring agents include natural flavoring agents (thaumatin, and *stevia* extracts such as rebaudioside A, glycyrrhizin, etc.) and synthetic flavoring agents (saccharin, aspartame, etc.).

When the food composition of the present disclosure is prepared as a beverage, it may further comprise citric acid, liquid fructose, sugar, glucose, acetic acid, malic acid, fruit juice, *Eucommia ulmoides* extract, jujube extract, licorice extract, or the like, in addition to the active ingredient of the present disclosure.

According to another aspect of the present disclosure, the present disclosure provides a pharmaceutical composition for preventing or treating climacteric or menopausal symptoms, the pharmaceutical composition comprising: (i) one or more lactic acid bacteria selected from the group consisting of lactic acid bacteria of the genus *Bifidobacterium*, lactic acid bacteria of the genus *Lactobacillus*, and lactic acid bacteria of the genus *Lactococcus*; (ii) a prebiotic composition comprising isoflavone and a soybean germ extract; and (iii) a pharmaceutically acceptable carrier.

The contents related to the lactic acid bacteria and prebiotic composition in the pharmaceutical composition of the present disclosure are the same as those described above with respect to the "food composition for preventing or alleviating climacteric or menopausal symptoms" according to another aspect of the present disclosure, and thus description thereof is omitted to avoid overlapping.

As used herein, the term "preventing" means suppressing the development of a disorder, a disease, or symptoms caused by the disease in animals that have never been diagnosed as having such a disorder, disease or symptoms, but are prone to such a disorder, disease or symptoms.

As used herein, the term "treating" means suppression of the development of a disorde, a disease or symptoms, (ii)

alleviation of the disorder, disease or symptoms, or (iii) elimination of the disorder, disease or symptoms.

Examples of pharmaceutically acceptable carriers that are included in the pharmaceutical composition of the present disclosure include, but are not limited to, carbohydrate compounds (e.g., lactose, amylose, dextrose, sucrose, sorbitol, mannitol, starch, cellulose, etc.), gum acacia, calcium phosphate, alginate, gelatin, calcium silicate, microcrystalline cellulose, polyvinylpyrrolidone, cellulose, water, syrup, salt solution, alcohol, gum Arabic, vegetable oil (e.g. corn oil, cotton seed oil, soy milk, olive oil, coconut oil, etc.), polyethylene glycol, methyl cellulose, methylhydroxy benzoate, propylhydroxy benzoate, talc, magnesium stearate, and mineral oil, which are generally used in formulation.

The pharmaceutical composition may further comprise a lubricant, a wetting agent, a sweetening agent, a flavoring agent, an emulsifying agent, a suspending agent, a preservative, and the like, in addition to the above-described components. Suitable pharmaceutically acceptable carriers and formulations are described in detail in Remington's Pharmaceutical Sciences (19$^{th}$ ed., 1995).

The suitable dose of the pharmaceutical composition of the present disclosure may vary depending on factors, including a formulation method, the mode of administration, the patient's age, body weight, sex, disease condition and diet, the duration of administration, the route of administration, excretion rate, and responsiveness to the drug. Meanwhile, the oral dose of the pharmaceutical composition of the present disclosure is preferably 0.001 to 1,000 mg/kg (body weight)/day.

The pharmaceutical composition of the present disclosure may be prepared in single-dose forms or in multi-dose packages using a pharmaceutically acceptable carrier and/or excipient according to a method that may be easily carried out by those skilled in the art. Here, the formulation of the pharmaceutical composition may be a solution, suspension or emulsion in oil or aqueous medium, or an extract, powder, granule, tablet or capsule, and may further comprise a dispersing agent or a stabilizer.

BRIEF DESCRIPTION OF THE DRAWINGS

FIGS. 7a and 7b show the results of measuring the hematological parameters of each experimental group in OVX rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.

FIGS. 9a to 9c show the results of measuring the bone parameters of each experimental group in OVX rats.

DESCRIPTION OF SPECIFIC EMBODIMENTS

Figure 1A:
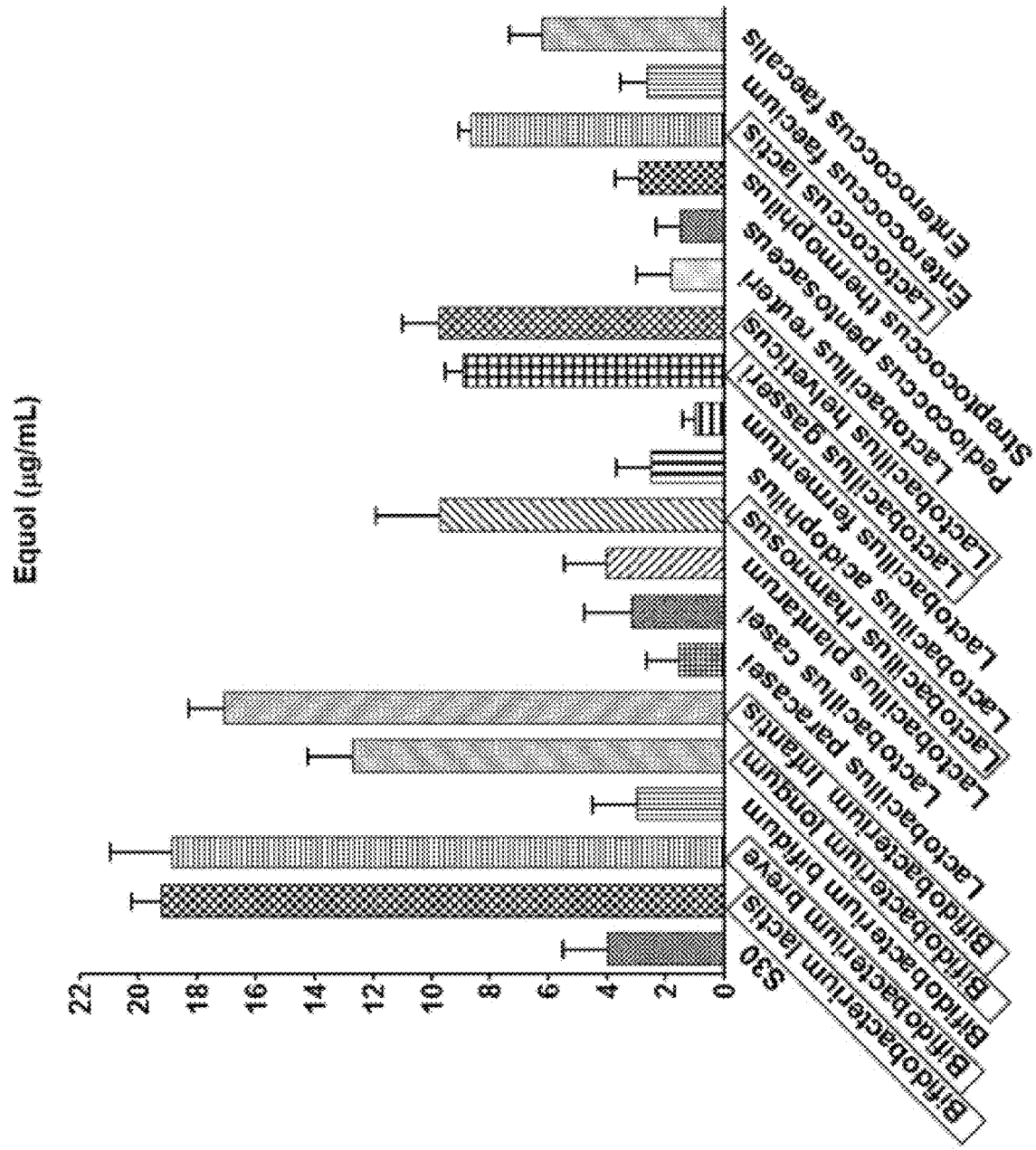
FIGS. 1a and 1b show the results of measuring the equol productivities of probiotic lactic acid bacteria in a soybean germ extract.

The specific embodiments described herein are representative of preferred embodiments or examples of the present disclosure, and thus the scope of the present disclosure is not limited thereto. It will be apparent to those skilled in the art that modifications and other uses of the present disclosure do not depart from the scope of the present disclosure as defined in the appended claims.

EXAMPLES

Experimental Methods

Experimental Example 1: Selection of Probiotics Having Ability to Convert Isoflavone into Equol A probiotic strain having the ability to produce equol from a soybean germ extract (S30) containing 30 wt % of isoflavone was selected.

First, a soybean germ extract was prepared using 40 g/L of a soybean germ extract (S30, prepared by Seorim Bio) containing 30 wt % of isoflavone and sterile water. The pH of the soybean germ extract was adjusted to 6.7 using 5M NaOH. The entire soybean germ extract was sterilized by autoclaving at 121° C. for 15 minutes. Microorganisms were activated in rehydrated MRS (Mann Rogosa Sharpe) broth (De Mann et al. 1960) at 37° C. for 20 hours three times, followed by fourth activation in the sterile soybean germ extract at an inoculum level of 5% (v/v). 40 to 400 mL of the sterile soybean germ extract was inoculated with the active culture (5% v/v), and incubated at 37° C. for 24 hours to hydrolyze isoflavone glycosides. The strain activated in the soybean germ extract was used.

In the initial screening step, incubation in the soybean germ extract was performed up to 48 hours, and whether equol was produced from the soybean germ extract was examined. In addition, samples were taken at regular time intervals in a time-dependent manner and measured for β-glucosidase activity. The measurement of β-glucosidase activity was performed using the p-nitrophenyl-β-D-glucopyranoside (pNPG) method. The sequence of the above screening steps was determined flexibly. That is, strains producing equol were first screened, and then β-glucosidase activity was measured, or strains having high β-glucosidase activity were first screened, and then whether the strains produced equol was examined. Screening was performed by measuring equol productivity and β-glucosidase activity in single strains or a combination of strains.

Experimental Example 2: In Vitro Cell Assay

Through an in vitro cell experiment, the estrogen-related efficacy of equol produced by probiotics and the expression levels of estrogen-related markers were examined. The expression levels of estrogen-related markers in MG-63 cells (*Homo sapiens* bone osteosarcoma, osteoblasts) and MCF-7 cells (human breast adenocarcinoma, breast cancer cells) were examined. Each of the cell lines was treated with the soybean germ extract culture of each probiotic strain selected based on equol formation and β-glucosidase activity, and the mRNA expression levels of biomarkers in the cell line were analyzed by real-time PCR (Table 1).

TABLE 1

| Gene | Organism | | Primer sequence |
|---|---|---|---|
| ERa | Human | Forward | AATTCAGATAATCGACGCCAG (SEQ ID NO:1) |
|  |  | Reverse | GTGTTTCAACATTCTCCCTCCTC (SEQ ID NO:2) |
| ERß | Human | Forward | TAG TGG TCC ATC GCC AGT TAT (SEQ ID NO:3) |
|  |  | Reverse | GGG AGC CAA CAC TTC ACC AT (SEQ ID NO:4) |
| pS2 | Human | Forward | CAT GGA GAA CAA GGT GAT CTG (SEQ ID NO:5) |
|  |  | Reverse | CAG AAG CGT GTC TGA GGT GTC (SEQ ID NO:6) |
| Osteocalcin | Human | Forward | ACA CTC CTC GCC CTA TTG (SEQ ID NO:7) |
|  |  | Reverse | GAT GTG GTC AGC CAA CTC (SEQ ID NO:8) |
| Alkaline phosphatase | Human | Forward | AAA CCG AGA TAC AAG CAC TCC CAC (SEQ ID NO:9) |
|  |  | Reverse | TCC GTC ACG TTG TTC CTG TTC AG (SEQ ID NO:10) |
| Collagen, type I, alpha 1 (COL1A1) | Human | Forward | GCG GCT CCC CAT TTT TAT ACC (SEQ ID NO:11) |
|  |  | Reverse | GCT CTC CTC CCA TGT TAA ATA GCA (SEQ ID NO:12) |
| BMP2 | Human | Forward | GCG TGA AAA GAG AGA CTG C (SEQ ID NO:13) |
|  |  | Reverse | CCA TTG AAA GAG CGT CCA C (SEQ ID NO:14) |

TABLE 1-continued

| Gene | Organism | Primer sequence |
|---|---|---|
| BMP4 | Human | Forward ACG GTG GGA AAC TTT TGA TGT G (SEQ ID NO:15)<br>Reverse CGA GTC TGA TGG AGG TGA GTC (SEQ ID NO:16) |
| Osteoprotegerin | Human | Forward GGA ACC CCA GAG CGA AAT ACA (SEQ ID NO:17)<br>Reverse CCT GAA GAA TGC CTC CTC ACA (SEQ ID NO:18) |
| β-actin | Human | Forward CATTGCCGACAGGATGCA (SEQ ID NO:19)<br>Reverse CATCTGCTGGAAGGTGGACAG (SEQ ID NO:20) |

2-1. Measurement of Estrogen Receptor (ER)-α,β Activation and Protein Expression Level A cell experiment was performed using MCF-7 cells (breast cancer cells), Ishikawa cells (endometrial cancer cells) and SaOS-2 cells (ostesarcoma cells), which are established cell lines of tissues in which estrogen receptors are largely distributed. These cells were treated with each test substance, and whether the test substance activated the receptor was examined, thereby evaluating the gene transcription activity. In addition, the protein expression levels of ERα (ESR1) and ERβ (ESR2) were measured by a cell assay or a Western blotting assay in an animal model, and the mRNA expression levels of ERα (ESR1) and ERβ (ESR2) were measured by RT-PCR (reverse transcription polymerase chain reaction).

2-2. Measurement of mRNA Expression Levels of ESR1 and pS2

ESR1 and pS2 are estrogen-responsive genes whose expression is increased by estrogen receptors. MCF-7 cells (breast cancer cells) were treated with each test substance, and whether the test substance exhibited estrogenic activity was evaluated by analyzing changes in the mRNA expression levels of the genes.

2-3. Measurement of Expression Levels of Bone Density Markers in Osteoblasts

The expression levels of OPG (osteoprotegerin), BMP-2 (bone morphogenetic protein 2), BMP-4 (bone morphogenetic protein 4), osteocalcin, alkaline phosphatase and the like as bone formation markers were measured. BMP4 (bone morphogenetic protein 4) is a bone morphogenetic protein known to have high osteoinduction capacity, and BMP2 (bone morphogenetic protein 2) is a gene that promotes bone formation, and increased expression of BMP2 indicates promoted bone formation. COL1A1 (collagen type I α1) is a major component of connective tissue, cartilage or the like, and activates the production of type 1 collagen. In addition, OPG is a protein produced in bone-forming osteoblasts and inhibits the action of osteoclasts.

Experimental Example 3: Animal Experimental Test

For the finally selected probiotic strains, the climacteric symptom inhibitory activity of each strain in climacteric model experimental animals was evaluated.

3-1. Experimental Design

As experimental animals, female Sprague-Dawley rats (initial body weight: 150 to 180 g/rat) were used (6 rats/group). The experiment was performed for 10 weeks (1 week: acclimation period; 1 week: recovery period after ovariectomization (OVX); and 8 weeks: test substance administration period). Estrogen (17β-estradiol, E2), the soybean germ extract (30% isoflavone, S30), probiotics (BL+BT+LGA+LH, Pro), and feed (AIN-93G, obtained by replacing soybean oil with corn oil) were administered. Estrogen (17β-estradiol, E2) was administered at a dose of 10 μg/kg three times a week, S30 was administered at a dose of 10 mg/kg every day, and probiotics were administered at a dose of $1 \times 10^7$ CFU/head every day. Table 2 below shows the animal experimental schedule.

TABLE 2

| Group | Week 1-0 | Week 0-1 | Week 1 | Week 2 | Week 3 | Week 4 | Week 5 | Week 6 | Week 7 | Week 8 |
|---|---|---|---|---|---|---|---|---|---|---|
| Sham | Acclimation | | AIN-93G | | | | | | | |
| OVX | | Ovariectomization (week 0) & acclimation | AIN-93G | | | | | | | |
| OVX + E2 | | | 8-week administration of AIN-93G + E2 | | | | | | | |
| OVX + Pro | | | 8-week administration of AIN-93G + Pro 8 | | | | | | | |
| OVX + S30 | | | 8-week administration of AIN-93G + S30 | | | | | | | |
| OVX + Pro + S30 | | | 8-week administration of AIN-93G + E2 + S30 | | | | | | | |

3-2. Experiment for Measurement

The body weight of each experimental group was measured every week. After 8 weeks of administration, the contents of serum estrogen and equol in the blood of each experimental group were measured. After 8 weeks of administration, fat distribution measurement and quantitative measurement of each rat's abdominal tissue were performed through micro-CT imaging.

The thickness of vaginal epithelial cells was measured through H & E staining of the vaginal epithelial cells. Through measurement of the uterus weight, it was confirmed that the uterus weight was reduced due to OVX and the menopausal model was well induced. In addition, whether the administered substance also affected the endothelium of the uterus was examined.

For hematological analysis, serum lipid levels were analyzed by measuring triglyceride, total cholesterol, LDL cholesterol, HDL cholesterol and free fatty acid levels. In addition, vasodilation was measured. It is known that estrogen acts to promote vasodilation and reduce blood lipid, and that an increase in the prevalence of cardiovascular diseases in climacteric women is associated with decreased estrogen levels. Accordingly, as parameters for measuring the cardiovascular health of climacteric women, serum total cholesterol, HDL-cholesterol, VLDL-cholesterol, LDL-cholesterol and triglyceride levels were measured, and markers of vasoconstriction and vasodilation were measured, such as endothelin-1, nitric oxide (NO) and endothelial nitric oxide synthase (eNOS).

BMD (bone mineral density) and BMC (bone mineral concentration) were measured. Whether the lowering of bone density due to estrogen deficiency can be mediated by administration of the test substance was evaluated by measuring the bone density in the climacteric animal model (OVX). The expression levels of bone density markers in osteoblasts were measured. In climacteric women, the expression levels of bone resorption markers are generally higher than those of bone formation markers. Bone resorption markers are markers that are released when osteoclasts gnaw at bone, and include deoxypyridinoline, pyridinoline, and type 1 collagen cross-linked telopeptide (NTX, CTX). As bone formation markers, osteocalcin, alkaline phosphatase and the like were measured. The efficacy-related markers in climacteric women are shown in Table 3 below.

Example 2: Measurement of β-Glucosidase Activity of Probiotics

Figure 2A:
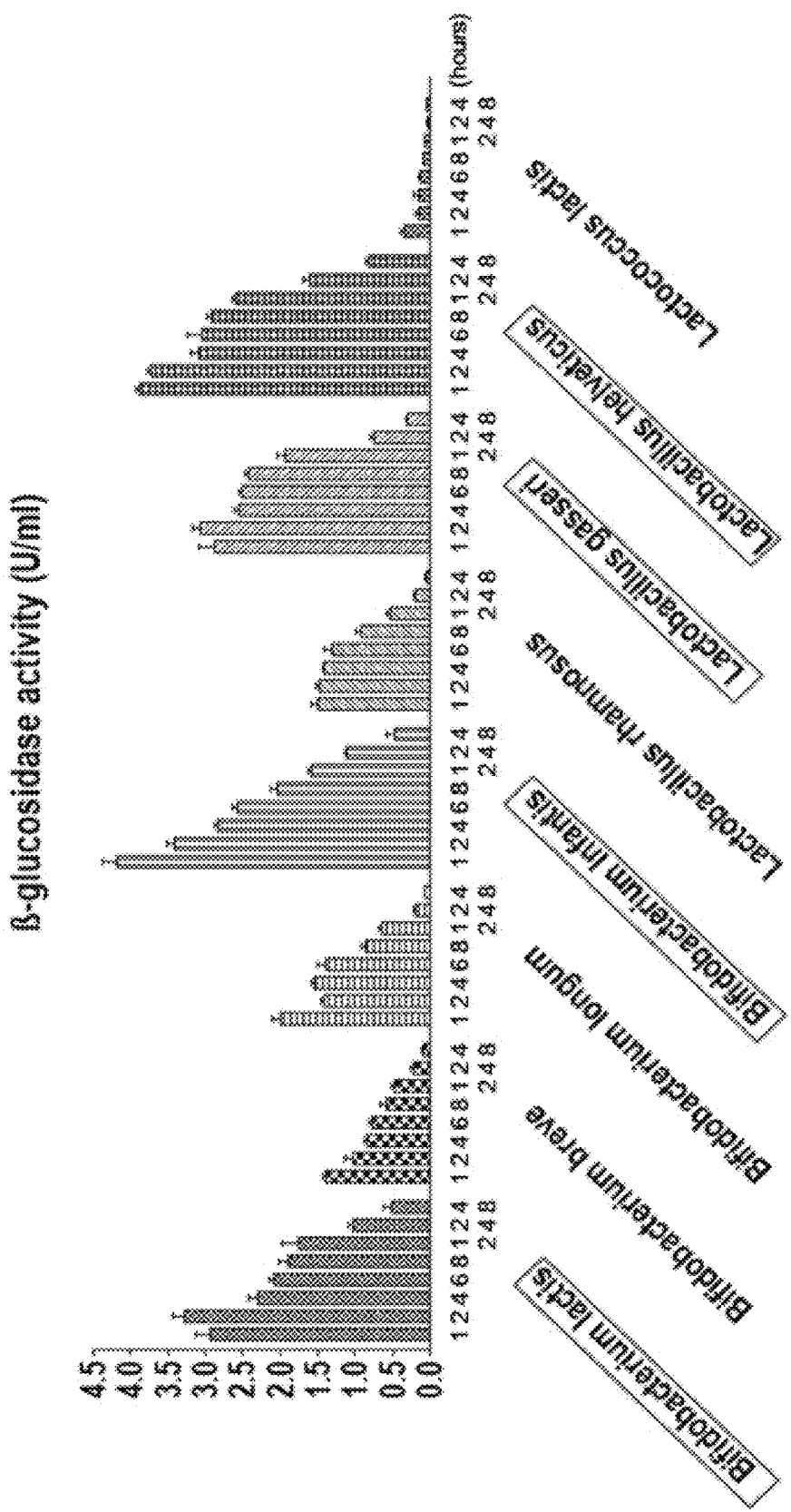
FIGS. 2a and 2b show the results of measuring the β-glucosidase activities of probiotic lactic acid bacteria in a soybean germ extract.
Figure 2B:
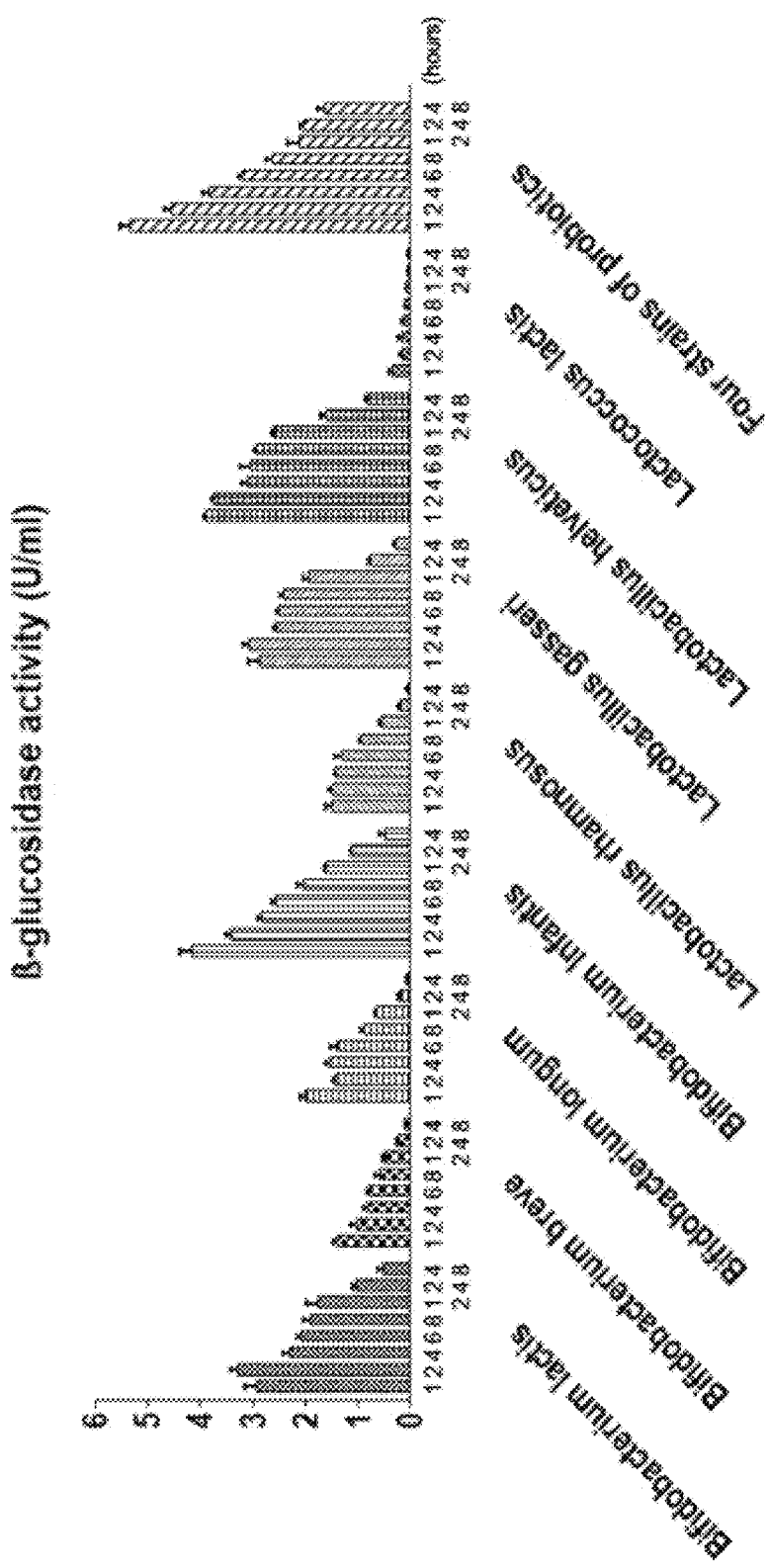

Isoflavones exist in the form of glycoside conjugates (sugar-bound glycosides). To form equol, glycosides bound to isoflavones should first be degraded into aglycones. This reaction is performed by the β-glycosidase of the gut microbiota. Among the eight equol-producing strains, strains having high efficiency were screened by measuring the β-glucosidase activity under the same conditions. In the initial reaction time period (1 hour to 2 hours), strains having relatively high β-glucosidase activity were *B. lactis, B. infantis, L. gasseri* and *L. helveticus*, and also maintained higher β-glucosidase activity than other strains for a total of 48 hours of the reaction (FIG. 2a). In addition, the combination of four strains (*B. lactis, B. infantis, L. gasseri* and *L. helveticus*) maintained higher β-glucosidase activity than other single strains (FIG. 2b). Four probiotics (*B. lactis, B. infantis, L. gasseri* and *L. helveticus*) were selected, which produced high concentrations of equol by reaction with the soybean germ extract (S30) in the gut after administration

TABLE 3

| | Biomarker | Product |
|---|---|---|
| Neurotransmitters | Serotonin | Rat 5-hydroxy tryptamine (5-ht) ELISA Kit |
| | Norepinephrine | Rat Norepinephrine (NE) ELISA Kit |
| Bone formation markers | Osteocalcin | Rat Osteocalcin (OC) ELISA Kit |
| | Alkaline phosphatase | Rat bone alkaline phosphatase, BALP ELISA Kit |
| Bone resorption markers | Deoxypyridinoline | Rat deoxypyridinoline (DPD) ELISA Kit |
| | Pyridinoline | Rat Pyridinoline (PYD) ELISA Kit |
| | NTX | Rat cross linked N-telopeptide of type I collagen, NTX ELISA Kit |
| | CTX | Rat cross Linked C-telopeptide of type I collagen (CTX-I) ELISA Kit |
| Cardiovascular markers | Endothelin-1 | Rat Endothelin 1 ELISA Kit |
| | Nitric oxide | Rat nitric oxide (NO) ELISA Kit |
| | eNOS | Rat Endothelial Nitric Oxide Synthase ELISA Kit |
| Follicle-stimulating Hormone | Follicle-stimulating hormone | Rat Follicle Stimulating Hormone (FSH) ELISA Kit |
| Luteinizing hormone | Luteinizing hormone | Rat Luteinizing hormone ELISA Kit |
| Estradiol | Estradiol, E2 | Rat Estradiol (E2) ELISA Kit |
| Equol | Equol | Equol ELISA Kit |

Experimental Results

Example 1: Measurement of Concentration of Equol Produced by Probiotics

Figure 1B:
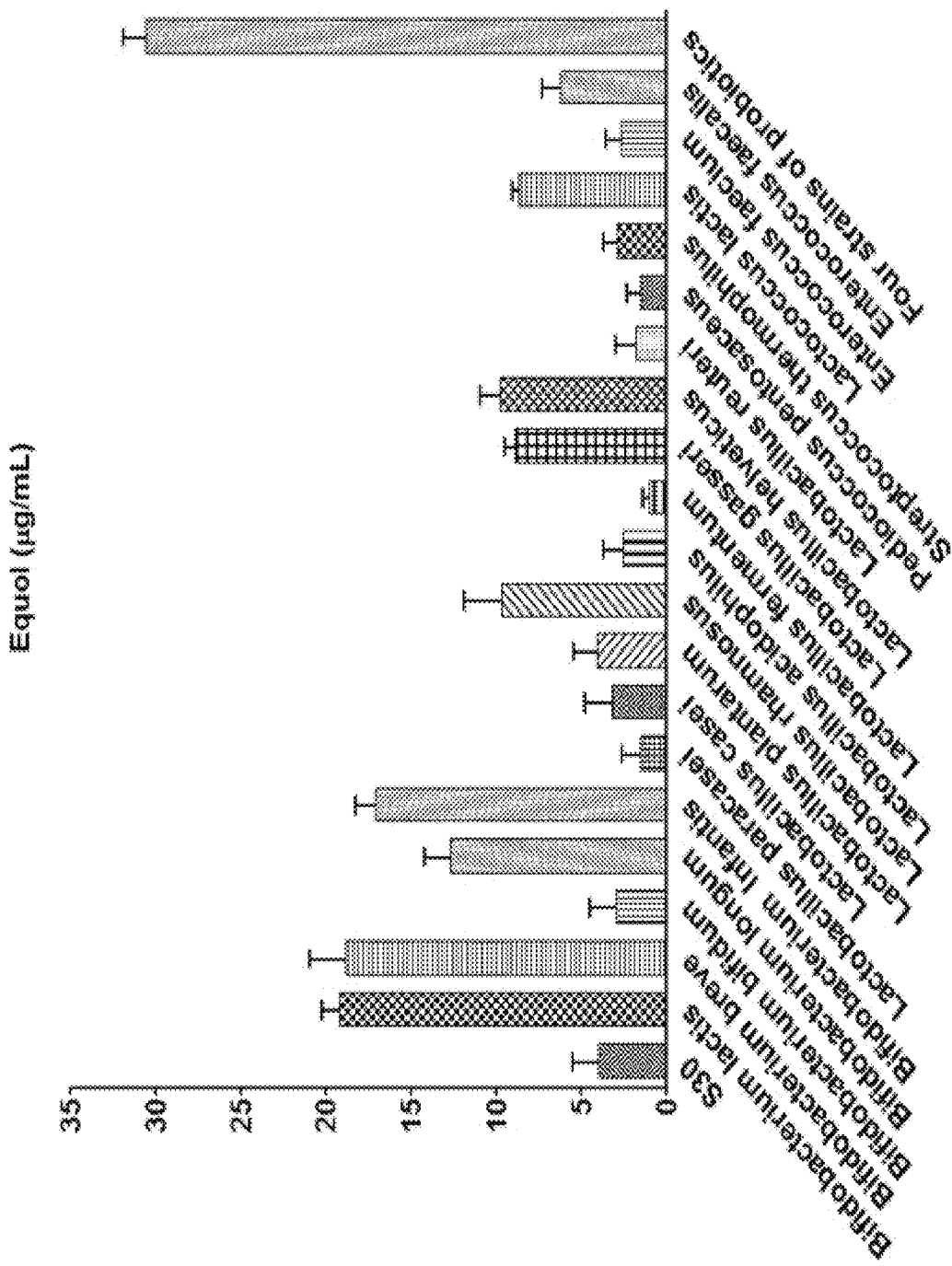

Each of the strains (19 CBT strains) held by Cell Biotech Co., Ltd. was inoculated into a 30% isoflavone-containing soybean germ extract (S30) and cultured at 37° C. for 48 hours, and then whether equol in the supernatant was produced and the concentration of equol were measured. As a result, it was confirmed that, in the culture supernatants of the eight strains (*Bifidobacterium lactis, Bifidobacterium breve, Bifidobacterium longum, Bifidobacterium infantis, Lactobacillus rhamnosus, Lactobacillus gasseri, Lactobacillus helveticus*, and *Lactococcus lactis*) measured, equol was produced and the significant concentration thereof was measured. In particular, in the strains of the genus *Bifidobacterium*, a large amount of equol was produced (FIG. 1a). In addition, a combination of four probiotic strains (*B. lactis, B. infantis, L. gasseri*, and *L. helveticus*), which has shown high equol productivity, showed higher equol productivity than each single strain (FIG. 1b).

and exhibited high β-glucosidase activity, and these selected probiotics were used in an in vivo test.

Figure 3A:
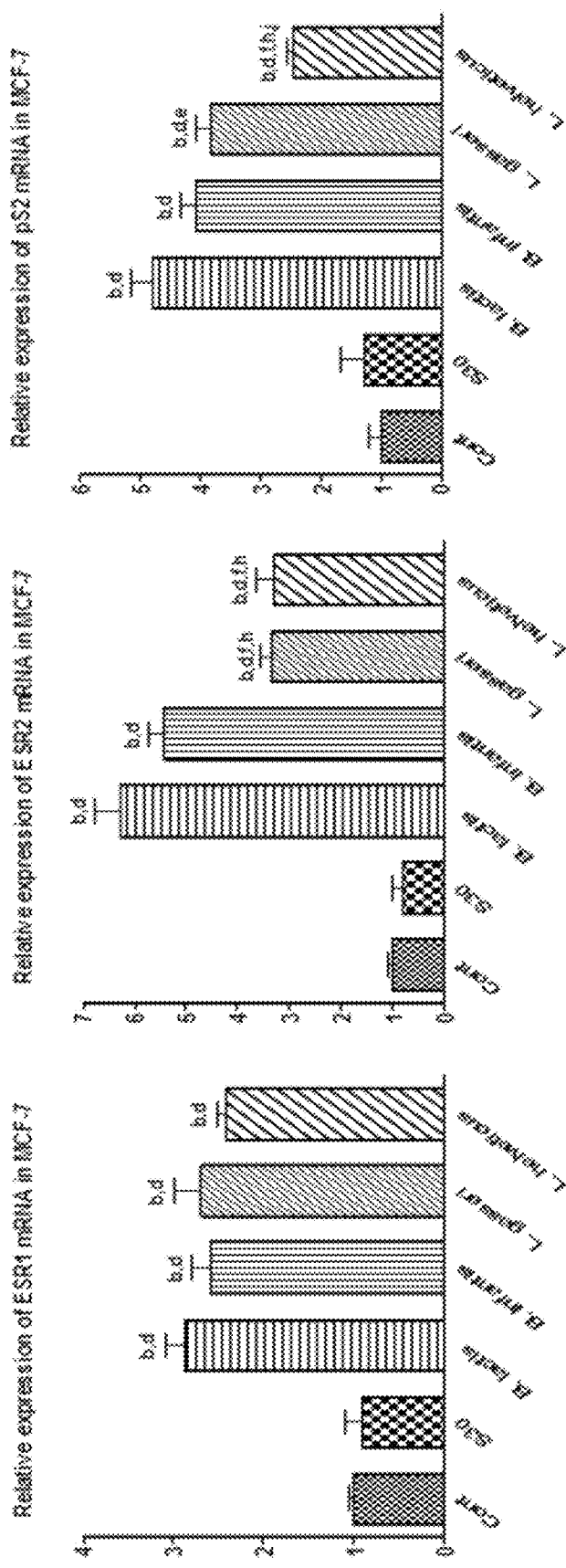
FIG. 3a shows the results of measuring the effect of treatment of MCF-7 cells either with S30 or with a culture obtained by culturing each of probiotic lactic acid bacteria strains (B. lactis, B. infantis, L. gasseri, and L. helveticus) in S30 on the mRNA expression levels of estrogen-related genes (ESR1, ESR2 and pS2).
Figure 3B:
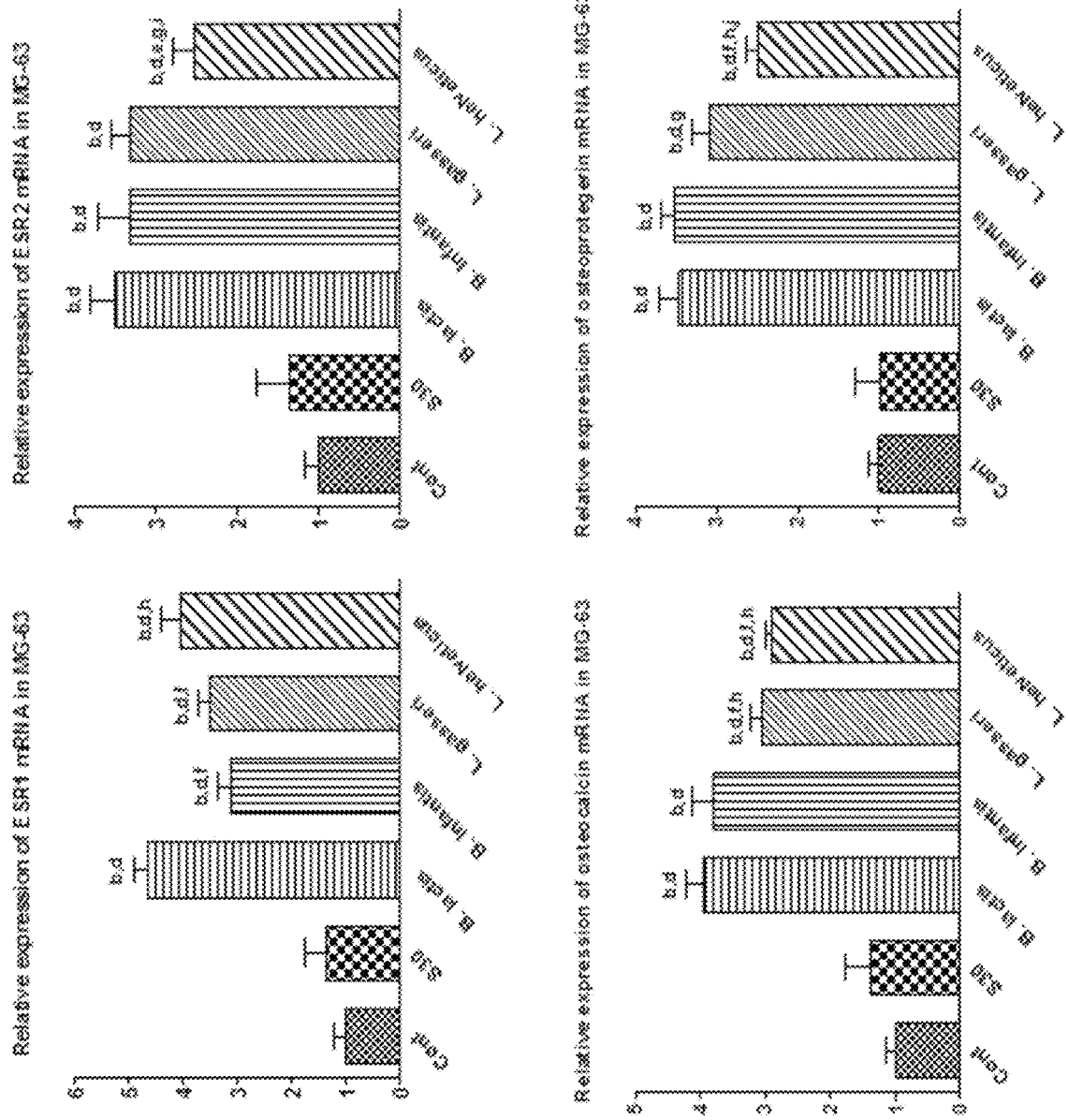
FIG. 3b shows the results of measuring the effect of treatment of MG-63 cells either with S30 ort with a culture obtained by culturing each of probiotic lactic acid bacteria strains (B. lactis, B. infantis, L. gasseri, and L. helveticus) in S30 on the mRNA expression levels of ESR1, ESR2, osteocalcin and osteoprotegerin.
Figure 3C:
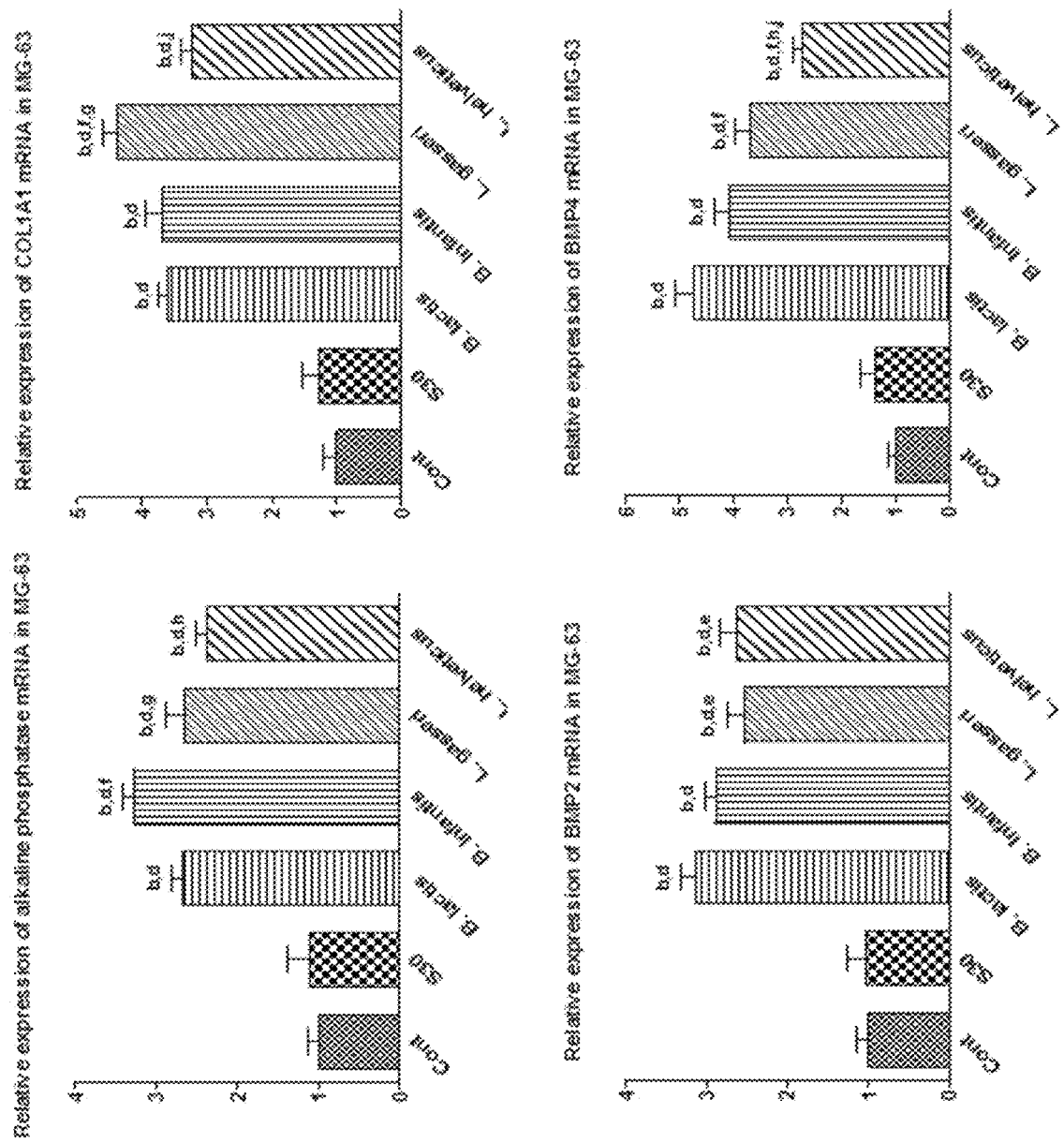
FIG. 3c shows the results of measuring the effect of treatment of MG-63 cells either with S30 or with a culture obtained by culturing each of probiotic lactic acid bacteria strains (B. lactis, B. infantis, L. gasseri, and L. helveticus) in S30 on the mRNA expression levels of alkaline phosphatase, COL1A1, BMP-2 and BMP-4.

Example 3: Measurement of Estrogen-Related Gene Expression in Breast Cancer Cells and Osteoblasts Each of MCF-7 cells (human breast adenocarcinoma, breast cancer cells) and MG-63 cells (*Homo sapiens* bone osteosarcoma, osteoblasts) was treated either with S30 or with the culture filtrate obtained by culturing each of the probiotic strains (*B. lactis, B. infantis, L. gasseri* and *L. helveticus*) in S30, and the expression levels of estrogen-related genes in the cells were measured. As a result of the measurement, it was confirmed that the expression levels of the genes in the cells treated with S30 alone did not significantly differ from those in the control group, but the expression levels of the genes in the cells treated with the culture filtrate obtained by culturing each probiotic strain in S30 did significantly differ from those in the control group, and the overall expression levels of the estrogen-related genes in these cells were significantly higher than those in the control group and the S30-treated group (FIGS. 3a to 3c).

Figure 4:
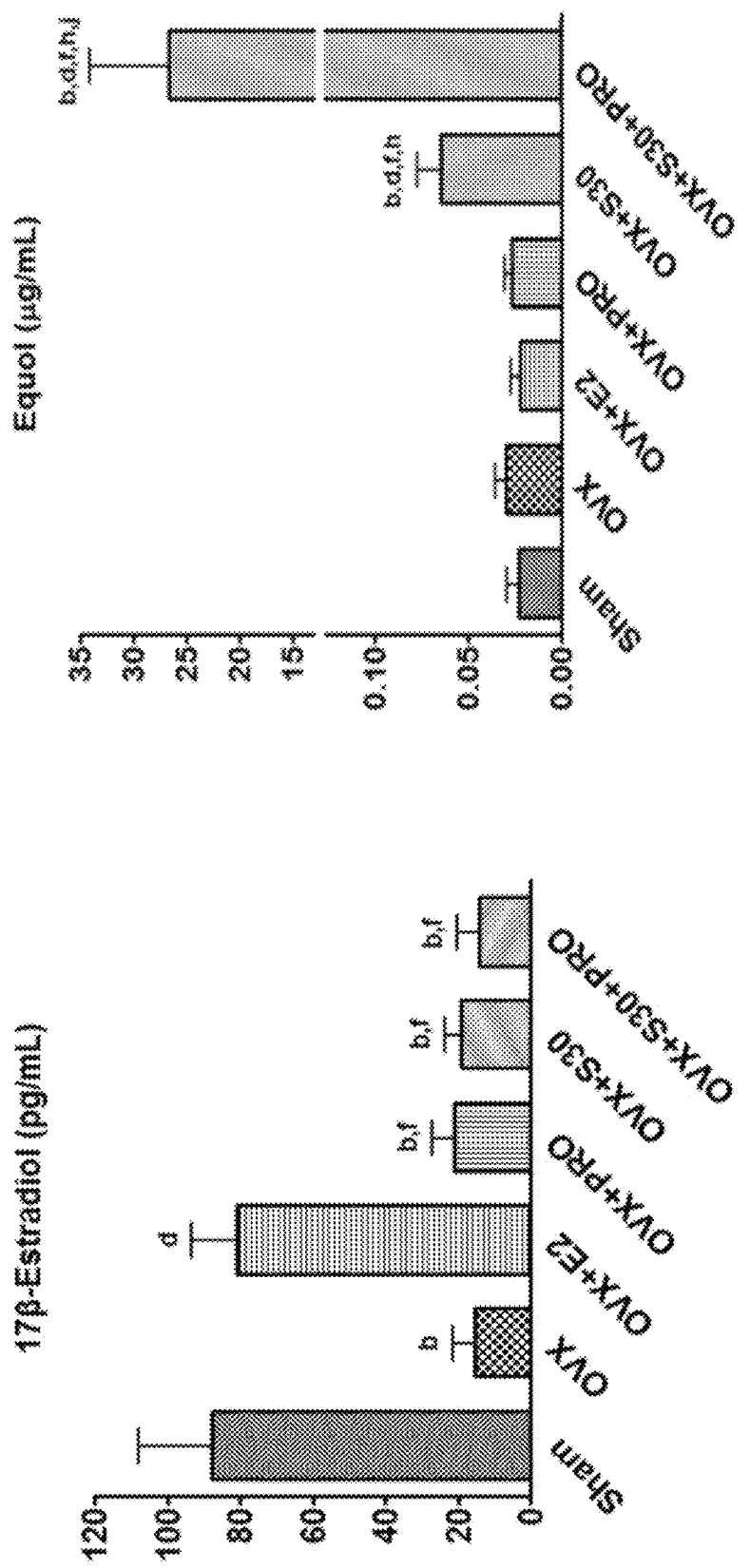
FIG. 4 shows the results of measuring the serum concentrations of 17β-estradiol and equol of each of experimental groups (Sham, OVX, OVX+E2, OVX+PRO, OVX+S30, and OVX+S30+PRO) in ovariectomized (OVX) rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.

Example 4: Measurement of Serum Concentrations of 17β-Estradiol and Equol in OVX Rats 17β-estradiol (E2) was measured in the serum of each experimental group, and as a result, it was confirmed that the serum concentration of 17β-estradiol was significantly low in the OVX group, but the serum concentration of 17β-estradiol in the OVX+E2 group to which 17β-estradiol was administered was similar to that in the Sham group. When each of probiotics, S30 and S30+probiotics was administered to the OVX rats, the serum concentration of 17β-estradiol did not significantly increase. Meanwhile, equol was measured in the serum of each experimental group, it was confirmed that the serum level of equol did not significantly differ between the Sham, OVX, OVX+E2, and OVX+probiotics groups, but administration of S30 or S30+probiotics significantly increased the serum concentration of equol. The increase in the serum level of equol in the OVX+S30 group was believed to be because equol was produced by the gut microbiota of the rats. Administration of S30+proiotics showed a significant increase in the serum level of equol, suggesting that administration of the probiotics to the gut microbiota of the rats exhibited a synergistic effect on the production of equol from S30 (FIG. 4).

Example 5: Measurement of Changes in Body Weight in OVX Rats

Figure 5:
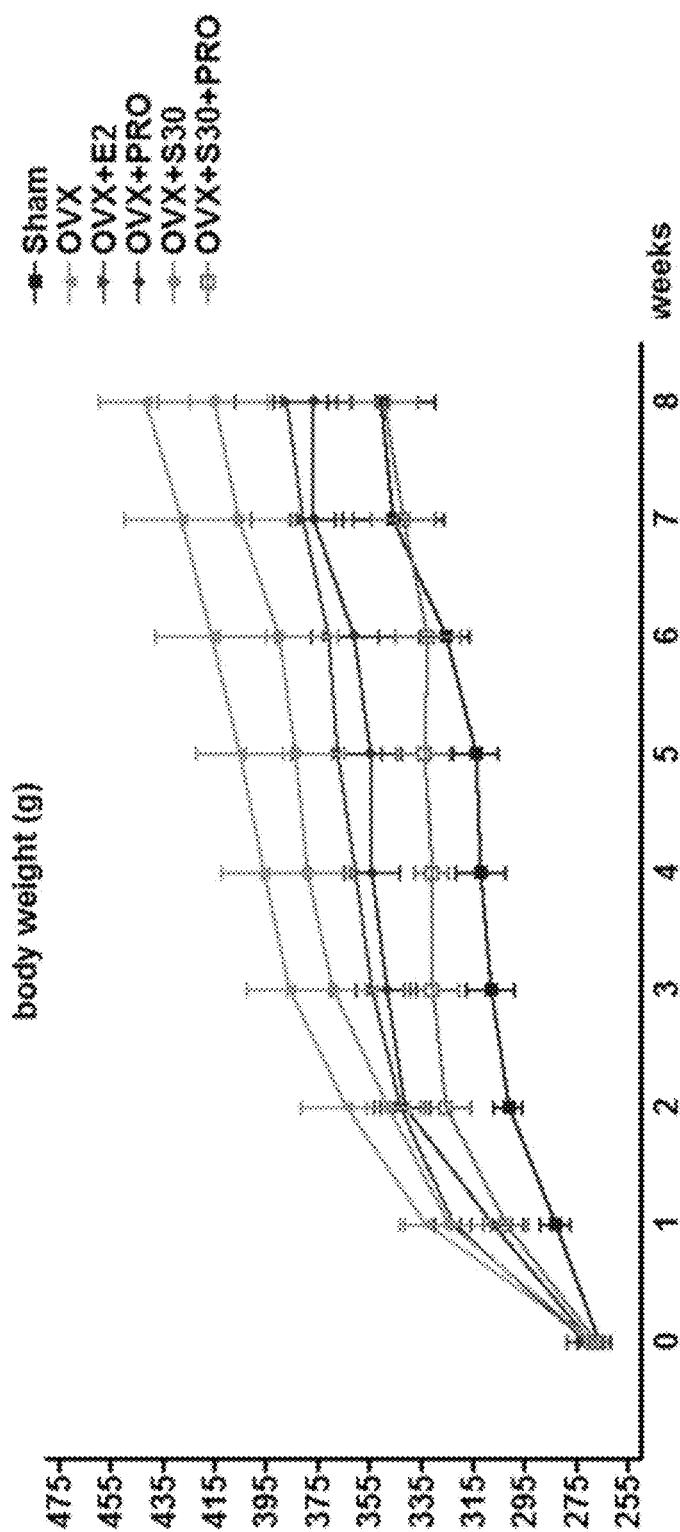
FIG. 5 shows the results of measuring changes in the body weight of each of experimental groups (Sham, OVX, OVX+E2, OVX+PRO, OVX+S30, and OVX+S30+PRO) in OVX rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.

Since a somewhat amount of estrogen is required even after menopause, estrogen precursors in the adipocytes and myocytes mainly in abdominal adipose tissue are converted into estrogen after menopause, and the adipocytes are activated in the process of compensating for the rapid decrease in estrogen caused by menopause, thus causing obesity. The body weights of the rats were measured over 8 weeks after ovariectomization (OVX). Before administration (0 week), the body weight values were similar without significant difference between the experimental groups. From 1 week after administration, a significant difference in the body weight between the experimental groups started to appear. The body weight gain caused by OVX compared to the Sham group started to appear, and particularly, the body weight gain significantly decreased in the S30+probiotics group. In addition, the effect of probiotic administration also appeared. From 3 weeks after the start of administration, a significant difference in the body weight of the S30+probiotics group from that of the Sham group started to not appear, and at 4 weeks after the start of administration, the body weight gain of the S30+probiotics group decreased compared to that of the E2 (17β-estradiol, estrogen)-administered group. At 8 weeks of administration (end of administration), it was confirmed that the body weight gain of the S30+probiotics group did not significantly differ from those of the Sham group and the probiotics-administered group, but significantly decreased compared to those of the OVX, E2 and S30 groups. In addition, it was confirmed that the body weights of the rats increased over 8 weeks after OVX, and that the administration of E2 significantly decreased the body weight gain of the rats. This effect was also observed upon administration of probiotics or S30+probiotics, but did not appear upon administration of S30 alone (FIG. 5).

Example 6: Measurement of Abdominal Fat Volume in OVX Rats

Figure 6A:
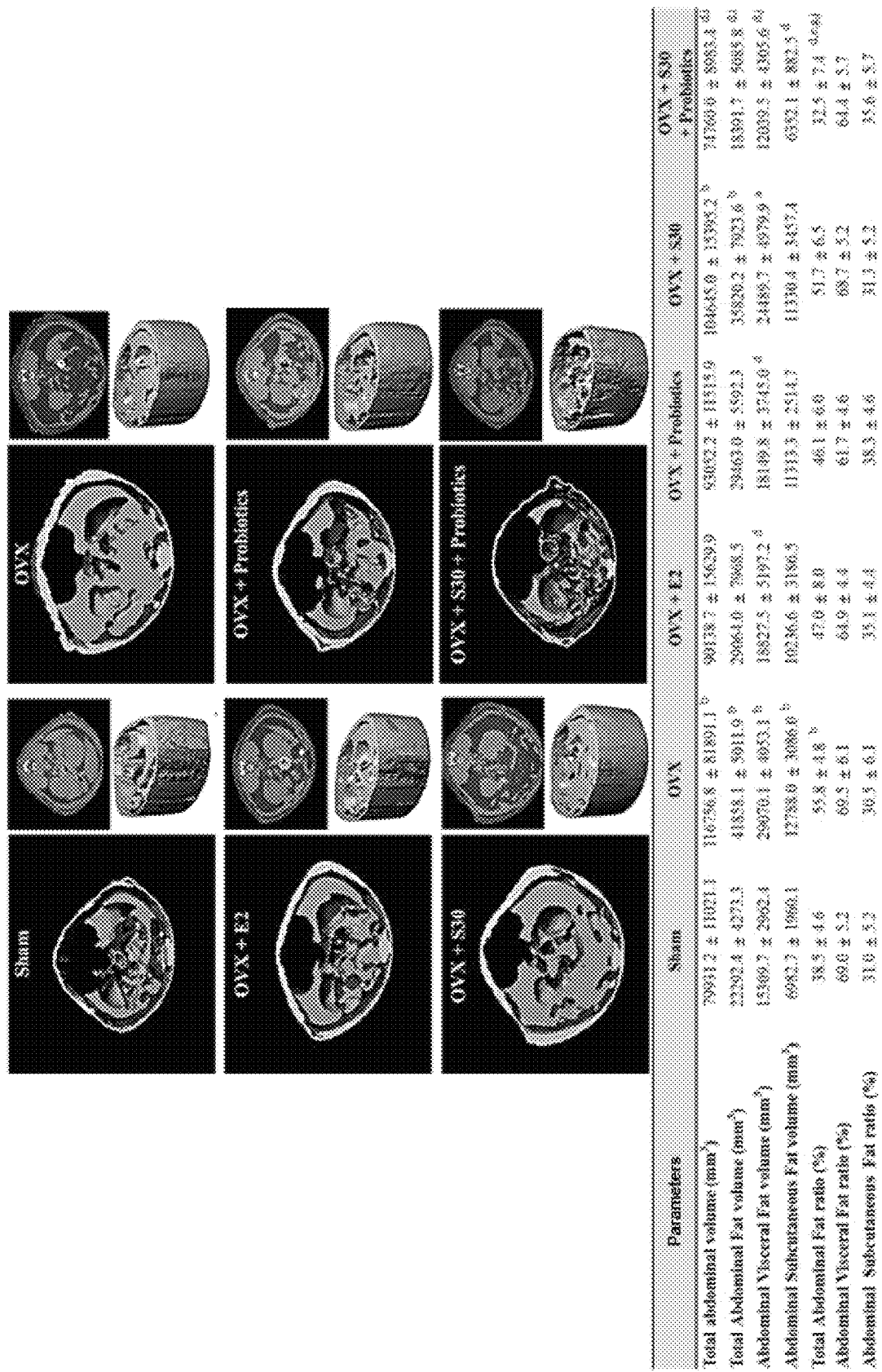
FIGS. 6a and 6b show the results of measuring the abdominal fat volume depending on the body weight of each experimental group in OVX rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.
Figure 6B:
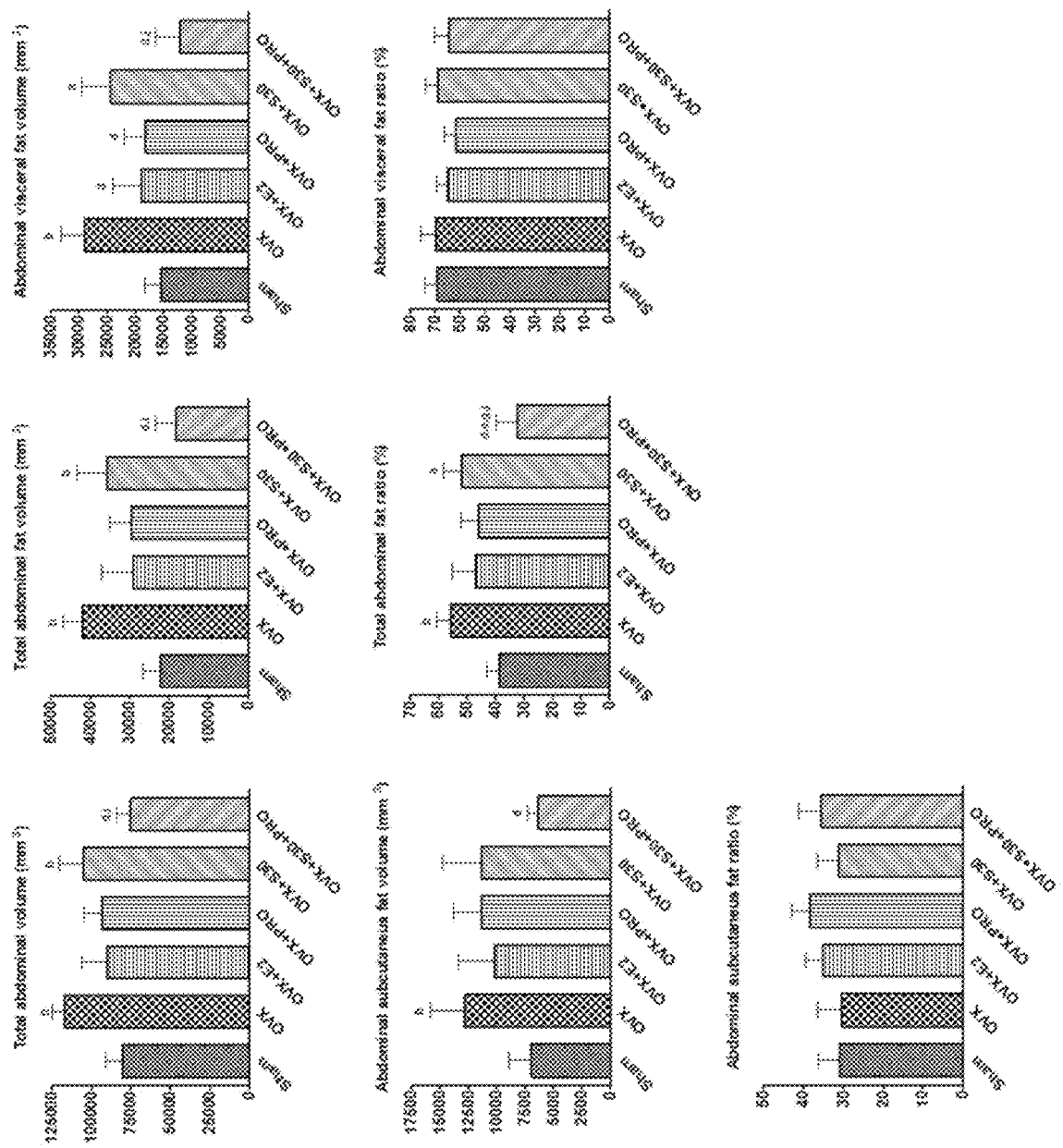

The abdominal fat volume depending on the body weight of each experimental group in the OVX rats was measured and compared (FIGS. 6a and 6b).

The results of measurement of the total abdominal volume indicated that OVX and administration of S30 alone more significantly increased the abdominal volume than Sham. Administration of E2 or probiotics showed no significant difference in the abdominal volume from OVX, but administration of S30+probiotics exhibited the effect of significantly decreasing the total abdominal volume compared to OVX.

In addition, the total abdominal fat volume (abdominal visceral fat volume+abdominal subcutaneous fat volume) was measured, and as a result, the results with the same tendency as in the measurement of the total abdominal volume were obtained. In addition, the abdominal visceral fat volume was measured, and as a result, it was confirmed that OVX and administration of S30 alone more significantly increased the abdominal visceral fat volume than Sham. Administration of E2 or probiotics more significantly decreased the abdominal visceral fat volume than OVX. Administration of S30+probiotics exhibited the effect of significantly decreasing the abdominal visceral fat volume compared to OVX and administration of S30.

The abdominal subcutaneous fat volume was measured, and as a result, it was confirmed that OVX significantly increased the abdominal subcutaneous fat volume compared to Sham. The abdominal subcutaneous fat volumes of other experimental groups did not significantly differ from that of the OVX group, but administration of S30+probiotics exhibited the effect of significantly decreasing the abdominal subcutaneous fat volume compared to OVX.

The total abdominal fat ratio (%) (total abdominal fat volume/total abdominal volume) significantly increased in OVX and administration of S30 alone compared to Sham. Administration of S30+probiotics showed no significant difference in the total abdominal fat ratio from Sham, and exhibited the effect of significantly decreasing the total abdominal fat ratio compared to administration of each of E2, probiotics and S30.

The results of measurement of the abdominal visceral fat ratio (%) (abdominal visceral fat volume/total abdominal fat volume) indicated that there was no significant difference in the abdominal visceral fat ratio between the experimental groups.

The results of measurement of the abdominal subcutaneous fat ratio (%) (abdominal subcutaneous fat volume/total abdominal fat volume (%) indicated that there was no significant difference in the abdominal subcutaneous fat ratio between the experimental groups.

Example 7: Measurement of Hematological Parameters in OVX Rats

Figure 7A:
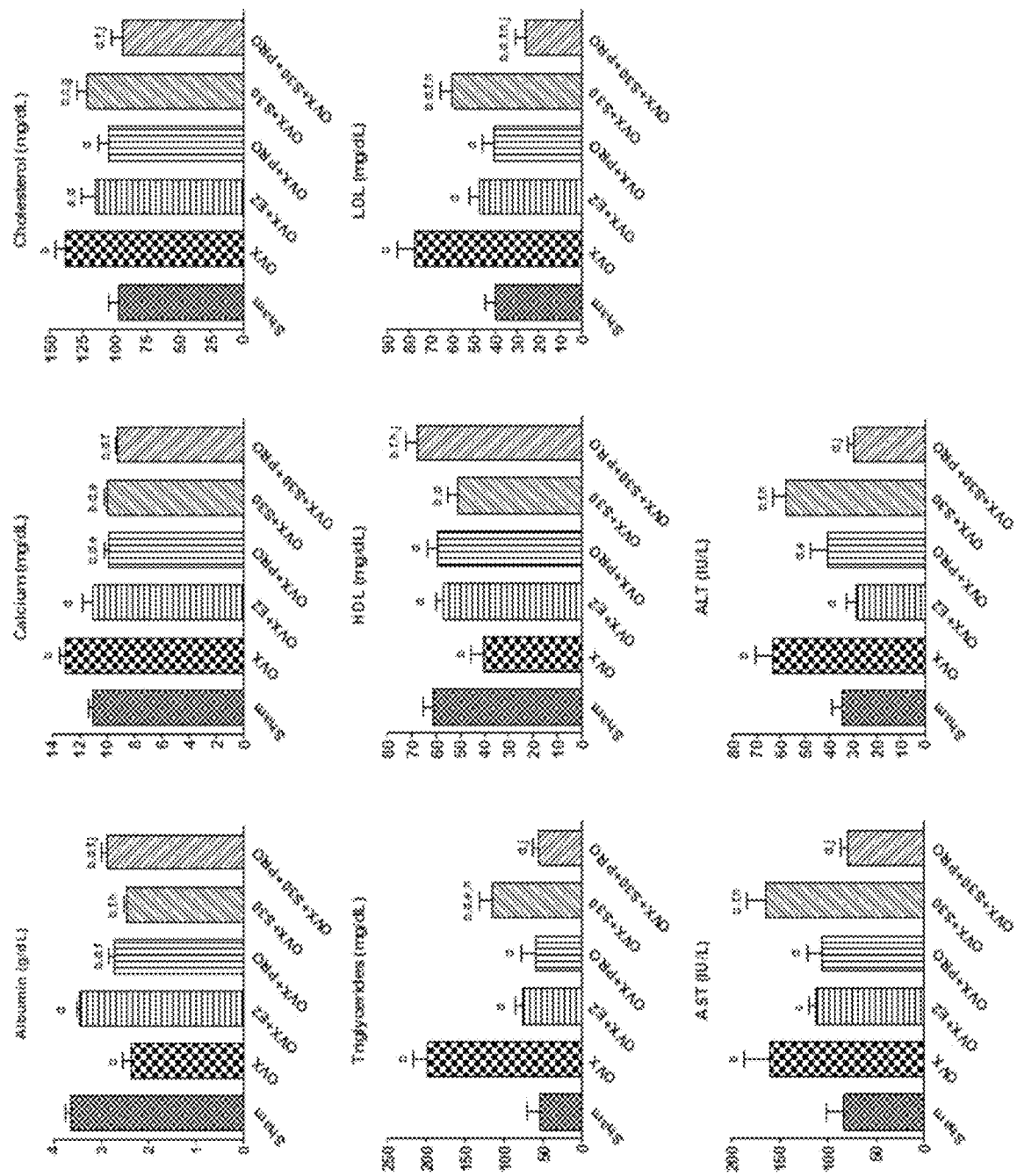

The hematological parameters of each experimental group in the OVX rats were measured and compared (FIGS. 7a and 7b).

Albumin acts as a carrier for several hormones, and binds to and transports electrolytes, such as Ca, P and sulfur (S), and thyroid hormones. When the concentration of albumin is lowered, various functions decrease. The concentration of albumin decreased due to OVX, but increased significantly due to administration of probiotics or S30+probiotics.

Changes in the blood concentration of calcium are affected by calcium present in the bone, and the increase in bone resorption by ovariectomization causes a decrease in bone quality, resulting in an increase in the blood concentration of calcium. Thus, changes in the concentration of calcium are associated with bone resorption. The blood concentration of calcium was increased due to OVX, but decreased due to administration of E2. In addition, administration of each of S30, probiotics and S30+probiotics significantly decreased the concentration of calcium compared to administration of each of Sham and E2.

When the secretion of estrogen decreases, the function of inhibiting the activation of lipoprotein lipase is lowered, resulting in excessive accumulation of fat, and hyperlipidemia appears. OVX significantly increased the concentrations of cholesterol, triglycerides, and LDL compared to Sham, and significantly decreased the concentration of HDL. Administration of each of S30, probiotics and S30+probiotics generally exhibited the effect of significantly alleviating hyperlipidemia, and particularly, administration of S30+probiotics exhibited higher effects on a decrease in the blood concentration of LDL and an increase in the blood concentration of HDL than administration of the other test substances.

OVX significantly increased the hepatic AST (aspartate transaminase) and ALT (alanine transaminase) concentrations compared to the Sham group. Administration of probiotics alone exhibited the effect of significantly decreasing the AST and ALT concentrations, but administration of S30+probiotics exhibited a better effect than administration of S30 alone.

Figure 8A:
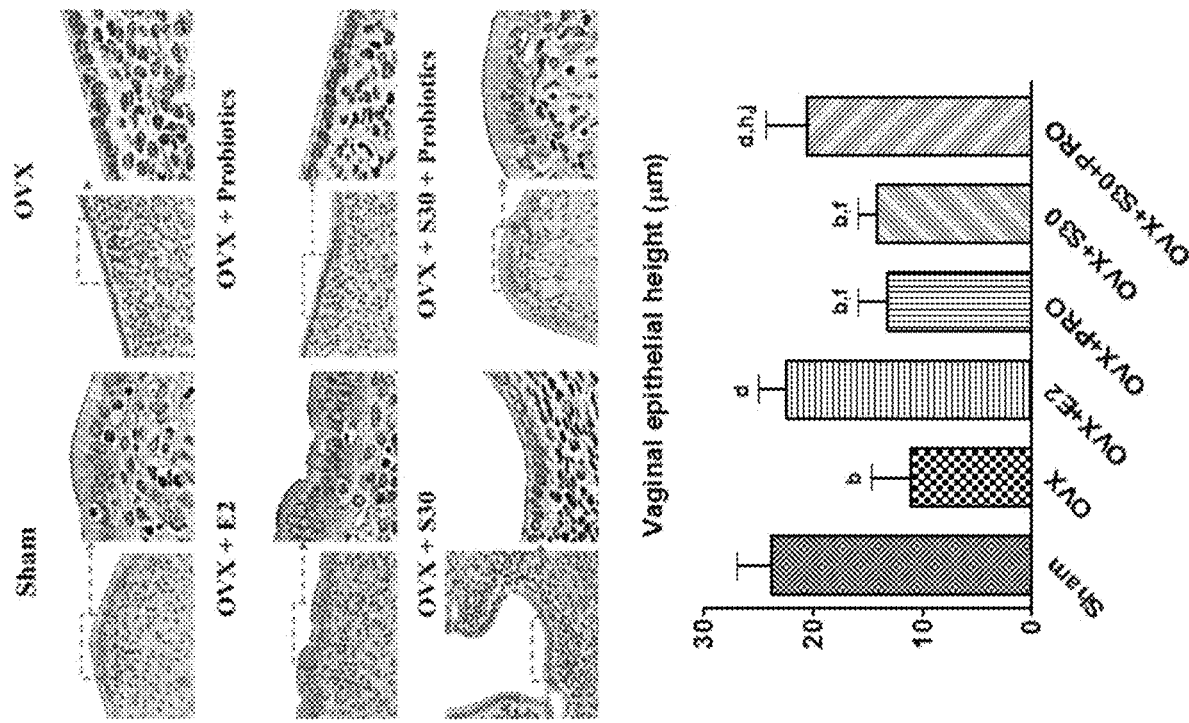
FIG. 8a shows the results of measuring the vaginal epithelial height of each experimental group in OVX rats.

Example 8: Measurement of Vaginal Endometrial Thickness in OVX Rats 8-1. Measurement of Vaginal Epithelial Height in Each Experimental Group The blood estrogen concentration that decreases after climacterium and menopause also affects the urogenital organs, causing redness of the vaginal mucosa, loss of elasticity, loss of wrinkles, changes in cell composition, and urogenital atrophy that results in an increase in vaginal acidity. As the thickness of vaginal epithelium and vaginal blood flow decrease, the vagina becomes dry, thinner, and pale, and the maturity of the vaginal epithelium decreases, resulting in increased immature cells. OVX significantly decreased the vaginal epithelial height compared to Sham, and administration of E2 more significantly increased the vaginal epithelial height than OVX. Administration of probiotics or S30 alone significantly decreased the vaginal epithelial height compared to Sham and administration of E2, and showed no significant difference from OVX. However, administration of S30+probiotics showed no significant difference in the vaginal epithelial height from the Sham and E2 groups, and more significantly increased the vaginal epithelial height than the OVX, probiotics or S30 group. This result is believed to be because administration of S30+probiotics exhibited a significant improvement effect against the change in vaginal tissue caused by a decrease in estrogen (FIG. 8a).

8-2. Measurement of Uterus Weight in Each Experimental Group

Figure 8B:
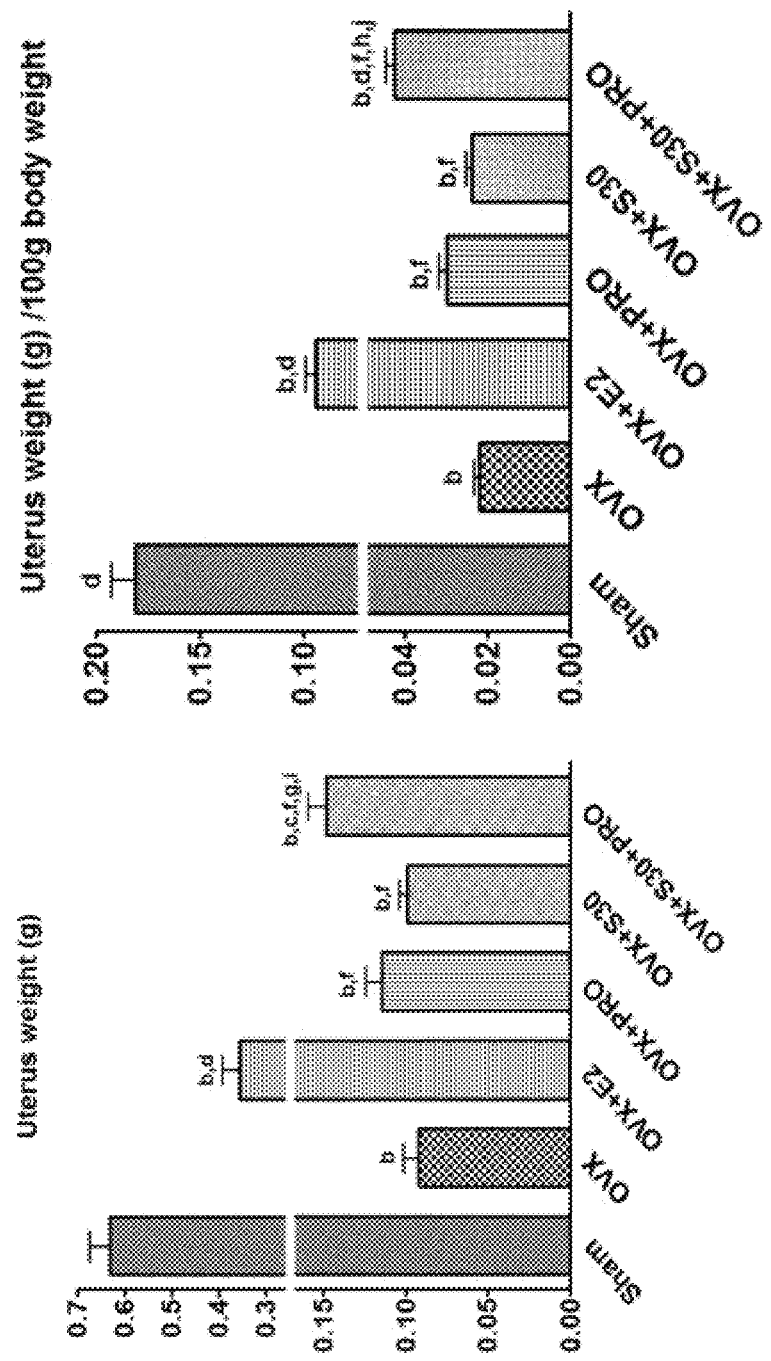
FIG. 8b shows the results of measuring the uterus weight of each experimental group in OVX rats. The measured values are expressed as mean±SD. a: $p<0.05$. b: $p<0.01$, compared to Sham group. c: $p<0.05$. d $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j $p<0.01$, compared to OVX+S30 group.

Ovariectomization (OVX) decreases the weight of the uterus by decreasing estrogen that causes the endometrium to grow. OVX significantly decreased the uterus weight compared to Sham, and administration of E2 more significantly increased the uterus weight than OVX. Administration of probiotics or S30 alone significantly decreased the uterus weight compared to Sham and administration of E2, and showed no significant difference in the uterus weight from OVX. However, administration of S30+probiotics significantly decreased the uterus weight compared to Sham and administration of E2, but significantly increased the uterus weight compared to that OVX or administration of probiotics or S30. These results suggest that administration of S30+probiotics exhibited a significant improvement effect against the change in uterus tissue caused by a decrease in estrogen (the uterus weight per 100 g body weight showed the same significance) (FIG. 8b).

Example 9: Measurement of Bone Parameters in OVX Rats

Figure 9A:
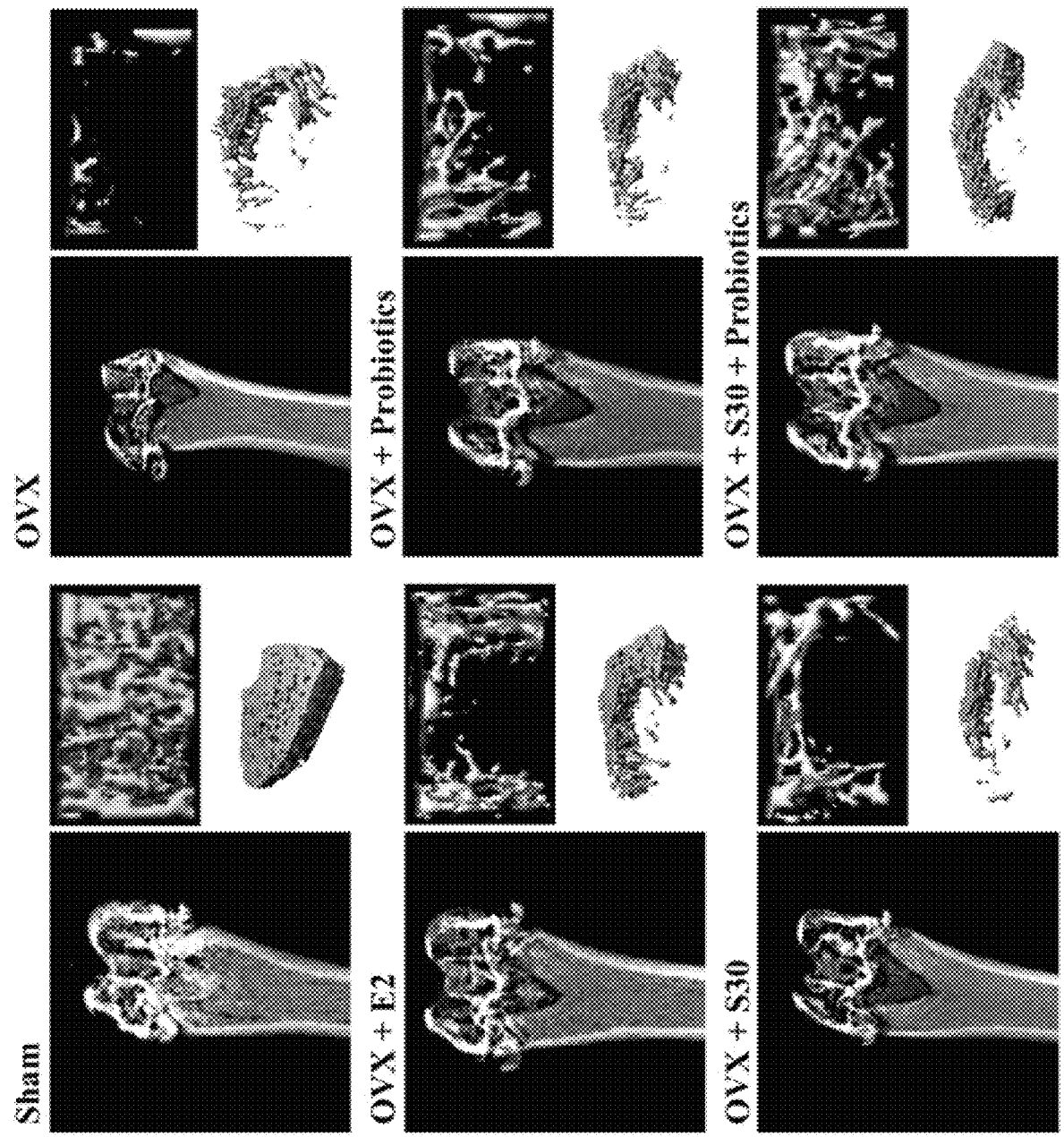
Figure 9B:
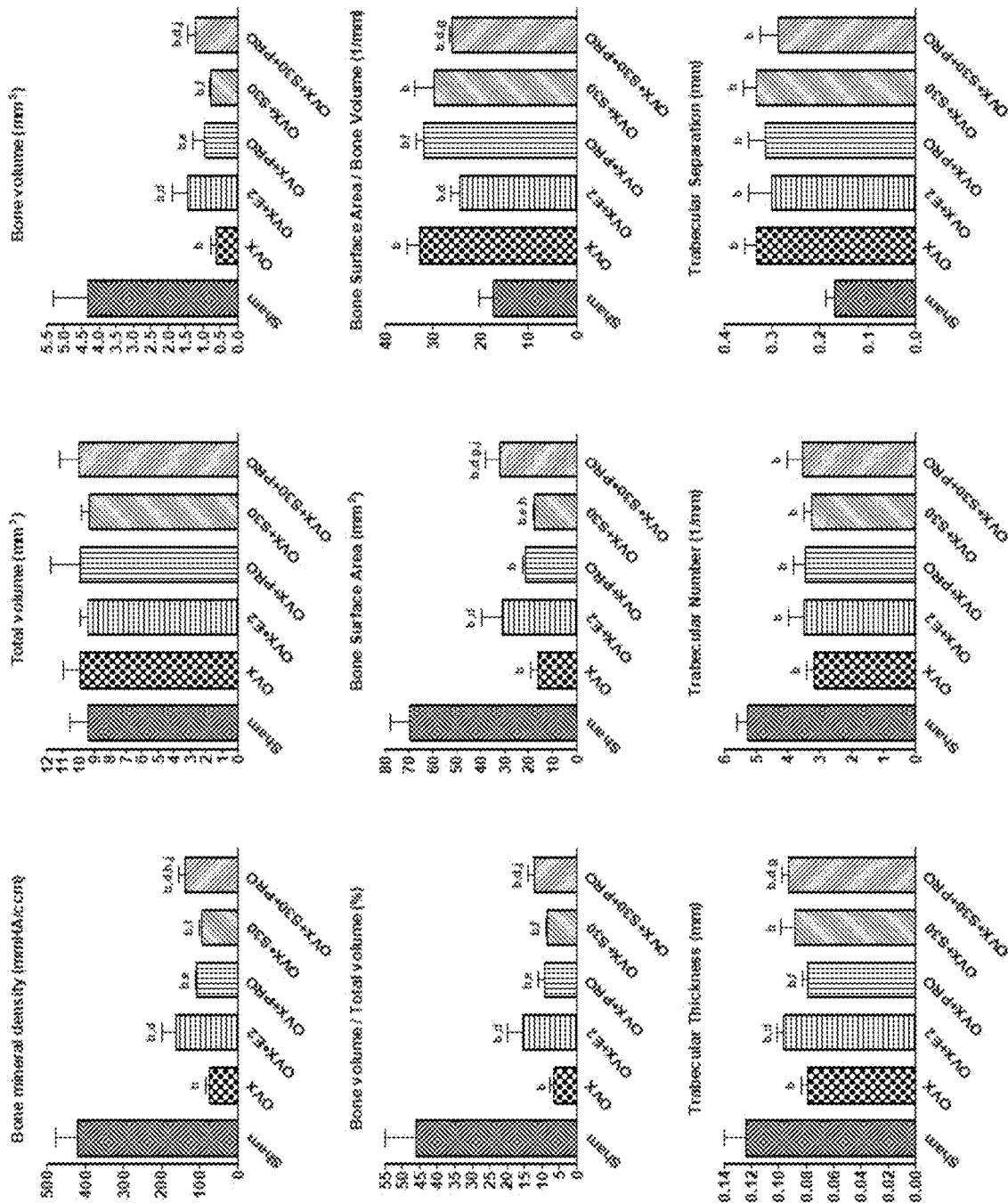

The bone parameters of each experimental group in the OVX rats were measured and compared (FIGS. 9a to 9c). BMD (bone material density) was significantly decreased by OVX. Administration of probiotics or S30 showed no significant difference in BMD from OVX, but administration of E2 or S30+probiotics significantly increased BMD. In particular, administration of S30+probiotics significantly increased BMD compared to administration of probiotics or S30. TV (total volume) was similar between all the experimental groups, and was not changed by OVX. OVX significantly decreased BV (bone volume), BV/TV, and BS (bone surface). Administration of probiotics or S30 showed no significant difference in BV, BV/TV and BS from OVX, but administration of E2 or S30+probiotics significantly increased BV, BV/TV and BS. BS/BV and Tb. Th (trabecular thickness) were significantly decreased by OVX and significantly increased by administration of each of E2 and S30+probiotics. Tb. N (trabecular number) and Tb. Sp (trabecular separation) significantly increased in all the experimental groups subjected to OVX, but did not significantly differ between the experimental groups.

Figure 10:
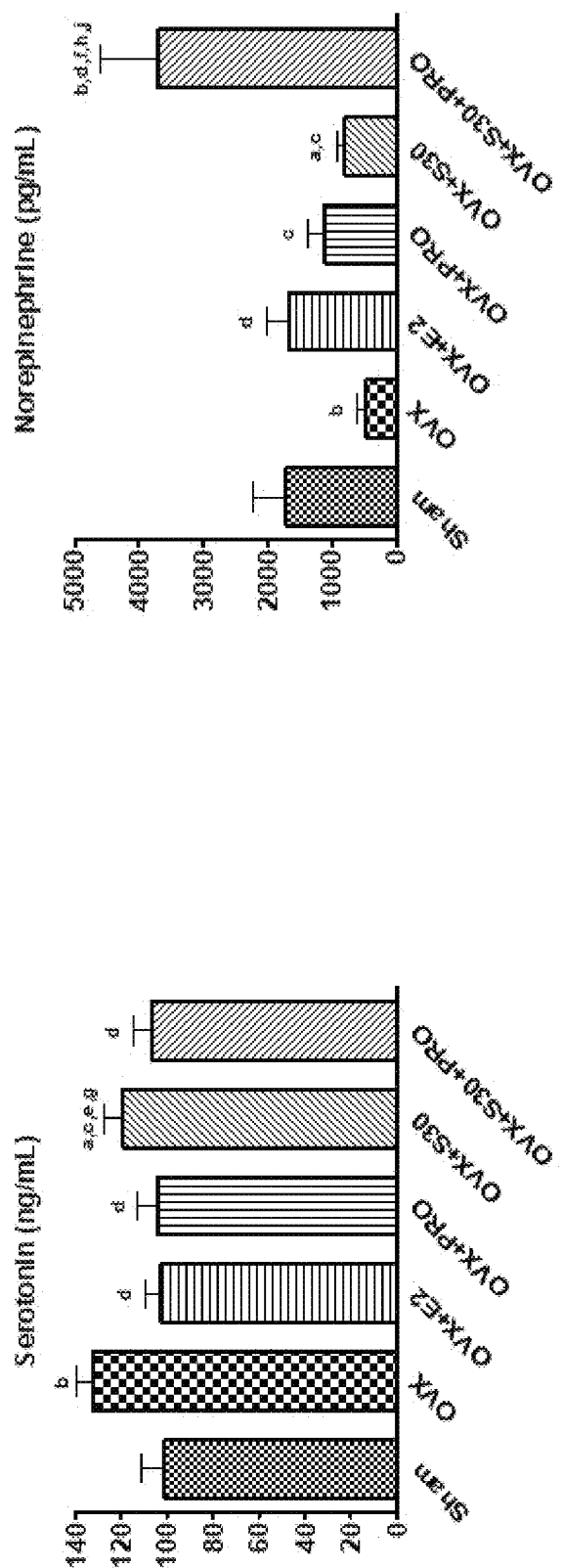
FIG. 10 shows the results of measuring the serum serotonine and norepinephrine concentrations of each experimental group in OVX rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.

Example 10: Measurement of Serum Concentrations of Serotonin and Norepinephrine in OVX Rats Serotonin is a neurotransmitter contained in the brain, visceral tissues, platelets, mast cells, etc., and peripheral serotonin that is produced in the visceral tissue under the influence of the microbiome inhibits differentiation of osteoblasts. Estrogen is known to increase the concentration of norepinephrine and receptors for neurotransmitters, and a decrease in norepinephrine may be induced in the climacteric period when estrogen decreases. The serum concentration of serotonin was measured, and as a result, it was confirmed that the serum concentration of serotonin was significantly increased by OVX compared to Sham, but was significantly decreased by administration of E2, probiotics or S30+probiotics. No significant difference between the S30 group and the S30+probiotics group appeared. The serum concentration of norepinephrine was measured, and as a result, it was confirmed that the serum concentration of norepinephrine was more significantly decreased by OVX than by Sham, but was significantly increased by administration of each of E2, probiotics, S30 and S30+probiotics. In particular, administration of S30+probiotics showed the highest significant increase in the serum concentration of norepinephrine (FIG. 10).

Figure 11A:
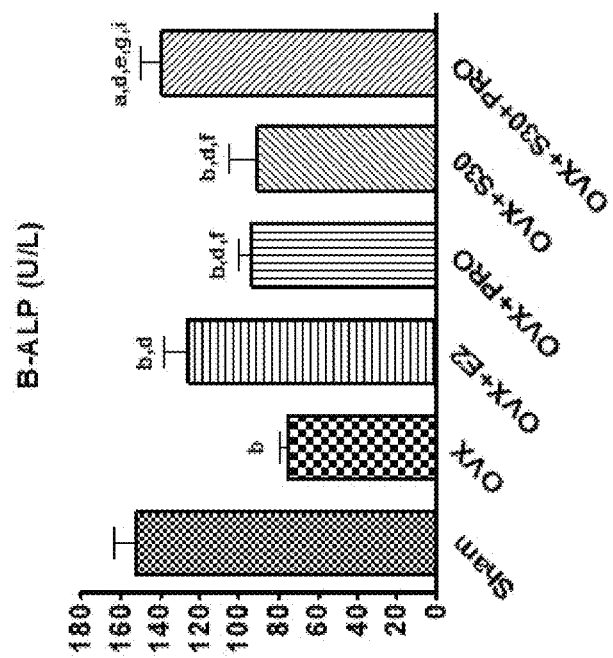
FIG. 11a shows the results of measuring the serum concentrations of bone formation markers (osteocalcin and B-ALP) of each experimental group in OVX rats. The measured values are expressed as mean±SD. a: $p<0.05$. b: $p<0.01$, compared to Sham group. c: $p<0.05$. d: $p<0.01$, compared to OVX group. e: $p<0.05$. f: $p<0.01$, compared to OVX+E2 group. g: $p<0.05$. h: $p<0.01$, compared to OVX+PRO group. i: $p<0.05$. j: $p<0.01$, compared to OVX+S30 group.
Figure 11A:
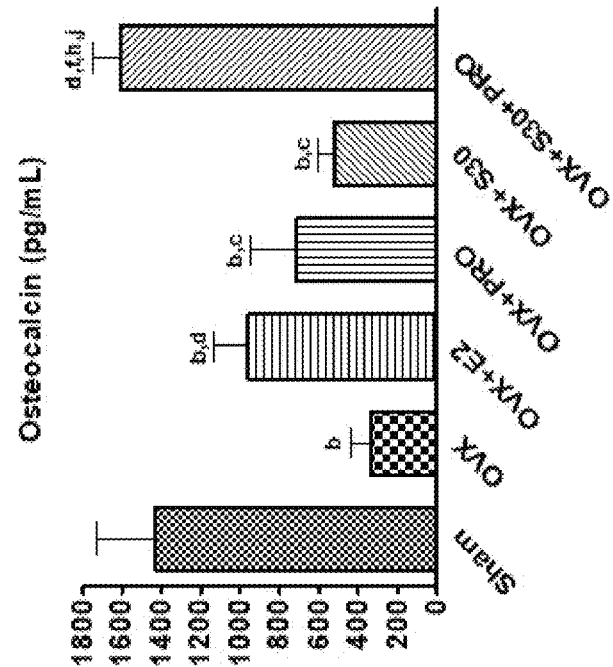
Figure 11B:
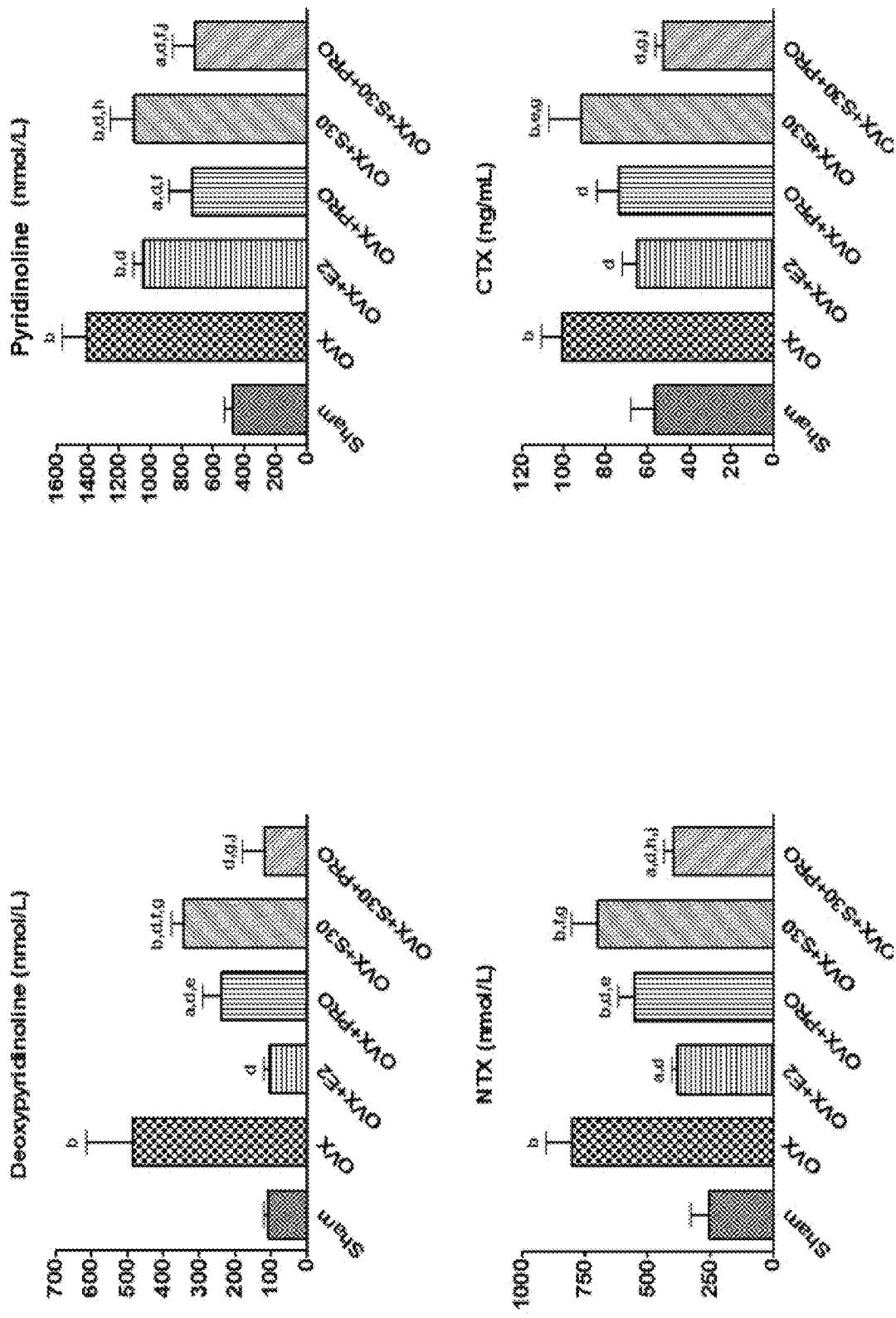
FIG. 11b shows the results of measuring the serum levels of bone resorption markers (deoxypyridinoline, pyridinoline, and type 1 collagen cross-linked telopeptide (NTX, CTX)) of each experimental group in OVX rats. The measured values are expressed as mean±SD. a: p<0.05. b: p<0.01, compared to Sham group. c: p<0.05. d: p<0.01, compared to OVX group. e: p<0.05. f: p<0.01, compared to OVX+E2 group. g: p<0.05. h: p<0.01, compared to OVX+PRO group. i: p<0.05. j: p<0.01, compared to OVX+S30 group.

Example 11: Measurement of Serum Concentrations of Bone Formation Markers and Bone Resorption Markers in OVX Rats Estrogen acts to inhibit bone resorption, and bone loss increases as estrogen secretion decreases in the climacteric period. In climacteric women, bone resorption markers generally significantly increase compared to bone formation markers. As bone resorption markers that are produced when osteoclasts degrade bone, deoxypyridinoline, pyridinoline, and type 1 collagen cross-linked telopeptide (NTX, CTX) were measured, and as bone formation markers, osteocalcin, bone alkaline phosphatase (B-ALP), etc. were measured. The results of measurement of the bone formation markers indicated that osteocalcin and B-ALP were significantly decreased by OVX, but were more significantly increased by administration of E2, probiotics or S30 than by OVX, and particularly, osteocalcin and B-ALP were more significantly increased by administration of S30+probiotics than by administration of E2, probiotics or S30 (FIG. 11a). The results of measurement of the bone resorption markers indicated that deoxypyridinoline, pyridinoline, NTX and CTX were generally increased by OVX, and were more significantly decreased by administration of E2, probiotics or S30 than by OVX, and particularly, these markers were significantly decreased by administration of S30+probiotics to levels achieved by administration of E2 (FIG. 11b).

Example 12: Measurement of Vascular Homeostasis Markers

Figure 12:
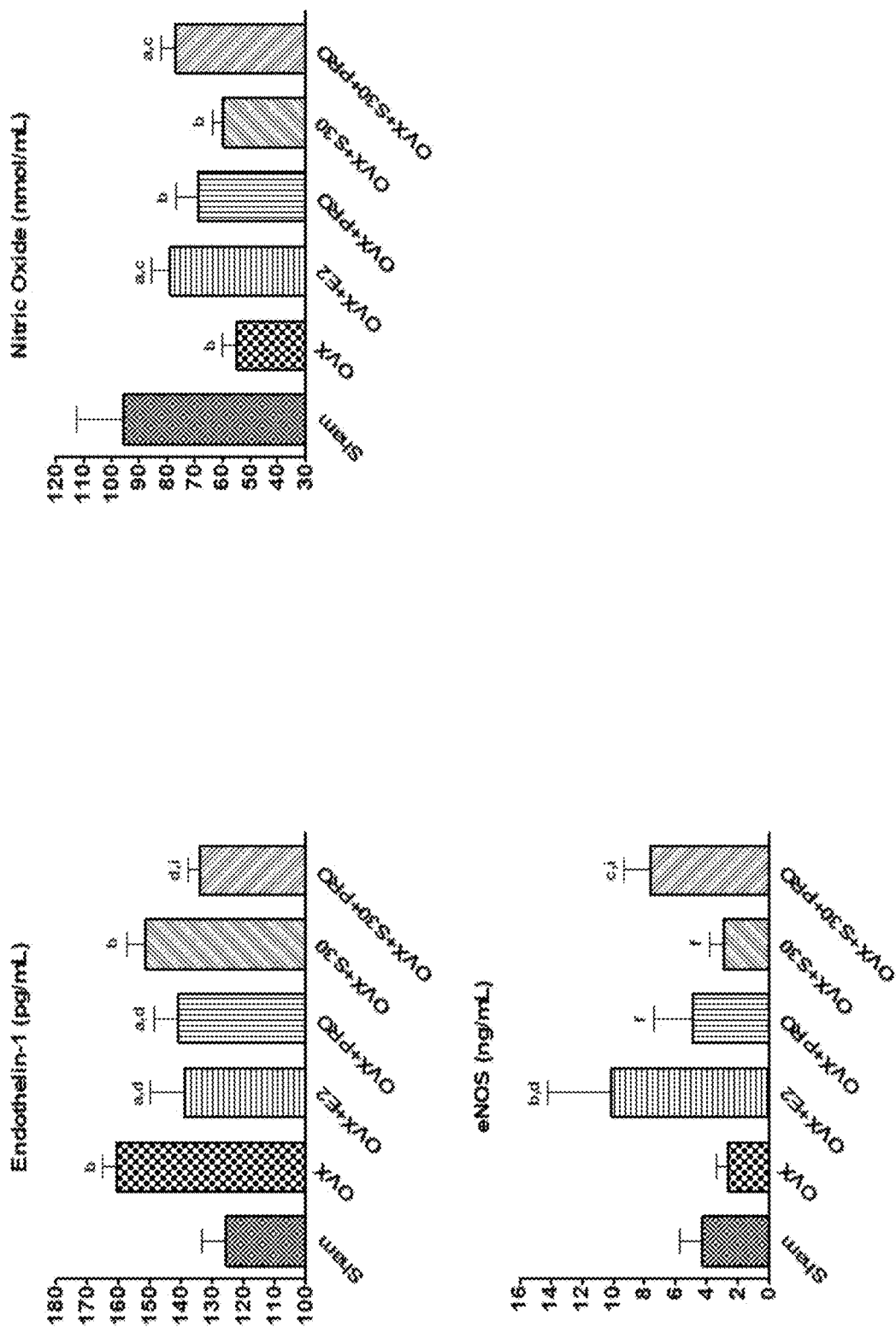
FIG. 12 shows the results of measuring the vascular homeostasis markers (endothelin-1, nitric oxide (NO) and endothelial nitric oxide synthase (eNOS)) of each experimental group in OVX rats. The measured values are expressed as mean±SD. a: p<0.05. b: p<0.01, compared to Sham group. c: p<0.05. d: p<0.01, compared to OVX group. e: p<0.05. f p<0.01, compared to OVX+E2 group. g: p<0.05. h p<0.01, compared to OVX+PRO group. i: p<0.05. j: p<0.01, compared to OVX+S30 group.

It is known that estrogen induces vasodilation and that an increase in the prevalence of cardiovascular diseases in climacteric women is associated with a decrease in estrogen levels. Accordingly, as markers for measuring the cardiovascular health of climacteric women, endothelin-1, which is a vasoconstriction marker, and nitric oxide (NO) and endothelial nitric oxide synthase (eNOS) which are vasodilation markers, were measured. The results of measurement of endothelin-1 indicated that endothelin-1 was significantly increased by OVX, but was more significantly decreased by administration of E2, probiotics or S30+probiotics than by OVX. In particular, the decrease in endothelin-1 by administration of S30+probiotics was similar to that shown by Sham, and endothelin-1 was more significantly decreased by administration of S30+probiotics than by administration of S30. NO (nitric oxide) was significantly decreased by OVX, but was more significantly increased by administration of E2 or S30+probiotics than by OVX, and administration of probiotics or S30 showed no significant difference in nitric oxide from OVX. Although there no significant difference in eNOS (endothelial nitric oxide synthase) between Sham and OVX, eNOS was significantly increased by administration of E2, and was more significantly increased by administration of S30+probiotics than by OVX. Administration of probiotics or S30 showed no significant difference in eNOS from Sham or OVX (FIG. 12).

Example 13: Measurement of Serum Levels of FSH and LH

Figure 13:
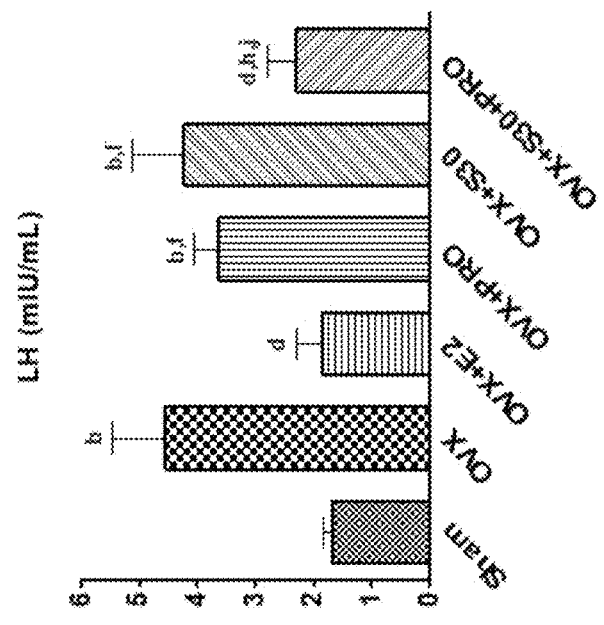
FIG. 13 shows the results of measuring the serum concentrations of follicle stimulating hormone (FSH) and luteinizing hormone (LH) of each experimental group in OVX rats. The measured values are expressed as mean±SD. a: p<0.05. b: p<0.01, compared to Sham group. c: p<0.05. d: p<0.01, compared to OVX group. e: p<0.05. f: p<0.01, compared to OVX+E2 group. g: p<0.05. h: p<0.01, compared to OVX+PRO group. i: p<0.05. j: p<0.01, compared to OVX+S30 group.
Figure 13:
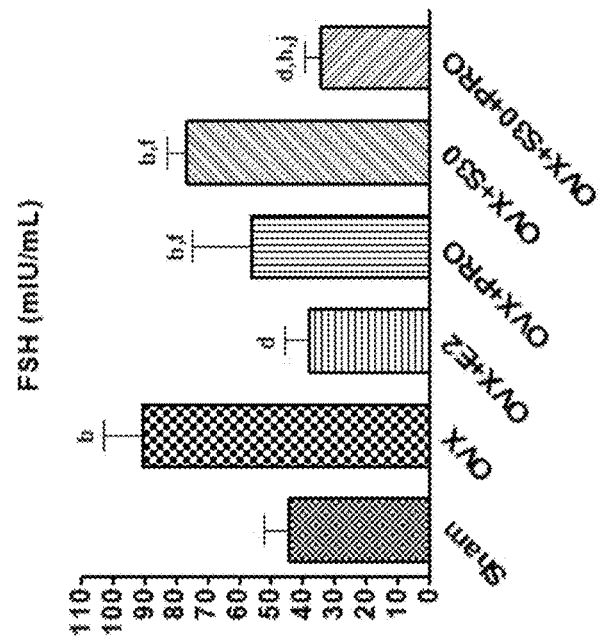

In the climacteric period, the secretion of estrogen is decreased due to the depletion of follicles in the ovary, and for this reason, the secretion of follicle stimulating hormone (FSH) and luteinizing hormone (LH) is increased by the negative feedback mechanism of the hypothalamus-pituitary axis. FSH (follicle stimulating hormone) was significantly increased by OVX. FSH was more significantly decreased by administration of E2 or S30+probiotics than by OVX. In particular, the level of FSH by administration of S30+probiotics was similar to that shown by Sham or administration of E2, and was significantly decreased compared to that shown by administration of probiotics or S30. LH (luteinizing hormone) showed a similar tendency to FSH, and administration of S30+probiotics exhibited a similar effect to administration of E2 (FIG. 13)

As described in detail above, the lactic acid bacteria of the present disclosure have β-glucosidase activity and a very excellent ability to convert isoflavones into equol compounds, and thus may exhibit estrogenic activity through synergism with the gut microbiota. Therefore, the lactic acid bacteria of the present disclosure may be effectively used for the prevention, relief or treatment of women's climacteric or menopausal symptoms.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto.

What is claimed is:

1. A food composition for preventing or alleviating climacteric or menopausal symptoms, the food composition consisting of:
   (i) lactic acid bacteria consisting of a combination of *Bifidobacterium lactis, Bifidobacterium infantis, Lactobacillus gasseri*, and *Lactobacillus helveticus*; and
   (ii) a prebiotic composition wherein the prebiotic composition is an isoflavone containing soybean germ extract, and wherein the isoflavone is comprised in an amount of 30 wt % based on the weight of the prebiotic composition.

2. The food composition of claim 1, wherein the climacteric or menopausal symptoms are hot flashes, night sweat, irregular menstrual cycles, loss of sexual desire, vaginal dryness, fatigue, hair loss, sleep disorder, attention difficulties memory loss, dizziness, weight gain, incontinence, abdominal bloating, allergies, brittle nails, changes in body odor, irregular heartbeats, depression, anxiety, restlessness, panic disorder symptoms, osteoporosis, osteopenia, hyperlipidemia, or dyslipidemia.

3. A pharmaceutical composition for preventing or treating climacteric or menopausal symptoms, the pharmaceutical composition consisting of:
   (i) lactic acid bacteria consisting of a combination of *Bifidobacterium lactis, Bifidobacterium infantis, Lactobacillus gasseri*, and *Lactobacillus helveticus*;
   (ii) a prebiotic composition wherein the prebiotic composition is an isoflavone containing soybean germ extract, and wherein the isoflavone is comprised in an amount of 30 wt % based on the weight of the prebiotic composition; and
   (iii) a pharmaceutically acceptable carrier.

4. The pharmaceutical composition of claim 3, wherein the climacteric or menopausal symptoms are hot flashes, night sweat, irregular menstrual cycles, loss of sexual desire, vaginal dryness, fatigue, hair loss, sleep disorder, attention difficulties memory loss, dizziness, weight gain, incontinence, abdominal bloating, allergies, brittle nails, changes in body odor, irregular heartbeats, depression, anxiety, restlessness, panic disorder symptoms, osteoporosis, osteopenia, hyperlipidemia, or dyslipidemia.

* * * * *

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Forward PCR primer for Er alpha gene

<400> SEQUENCE: 1
aattcagata atcgacgcca g                                        21

<210> SEQ ID NO 2
<211> LENGTH: 23
<212> TYPE: DNA
<213> ORGANISM: Artificial Sequence
<220> FEATURE:
<223> OTHER INFORMATION: Reverse PCR primer for Er alpha gene

<400> SEQUENCE: 2
gtgtttcaac attctccctc ctc                                      23

```
<210> SEQ ID NO 3
<211> LENGTH: 21
<212> TYPE: DNA
<213> ORGANISM: Artificial Sequence
<220> FEATURE:
<223> OTHER INFORMATION: Forward PCR primer for Er beta gene

<400> SEQUENCE: 3
tagtggtcca tcgccagtta t                                       21

<210> SEQ ID NO 4
<211> LENGTH: 20
<212> TYPE: DNA
<213> ORGANISM: Artificial Sequence
<220> FEATURE:
<223> OTHER INFORMATION: Reverse PCR primer for Er beta gene

<400> SEQUENCE: 4
gggagccaac acttcaccat                                         20

<210> SEQ ID NO 5
<211> LENGTH: 21
<212> TYPE: DNA
<213> ORGANISM: Artificial Sequence
<220> FEATURE:
<223> OTHER INFORMATION: Forward PCR primer for pS2 gene

<400> SEQUENCE: 5
catggagaac aaggtgatct g                                       21

<210> SEQ ID NO 6
<211> LENGTH: 21
<212> TYPE: DNA
<213> ORGANISM: Artificial Sequence
<220> FEATURE:
<223> OTHER INFORMATION: Reverse PCR primer for pS2 gene

<400> SEQUENCE: 6
cagaagcgtg tctgaggtgt c                                       21

<210> SEQ ID NO 7
<211> LENGTH: 18
<212> TYPE: DNA
<213> ORGANISM: Artificial Sequence
<220> FEATURE:
<223> OTHER INFORMATION: Forward PCR primer for Osteocalcin gene

<400> SEQUENCE: 7
acactcctcg ccctattg                                           18

<210> SEQ ID NO 8
<211> LENGTH: 18
<212> TYPE: DNA
<213> ORGANISM: Artificial Sequence
<220> FEATURE:
<223> OTHER INFORMATION: Reverse PCR primer for Osteocalcin gene

<400> SEQUENCE: 8
gatgtggtca gccaactc                                           18

<210> SEQ ID NO 9
<211> LENGTH: 24
<212> TYPE: DNA
<213> ORGANISM: Artificial Sequence
<220> FEATURE:
<223> OTHER INFORMATION: Forward PCR primer for Alkaline phosphatase
      gene
```

```
<400> SEQUENCE: 9
aaaccgagat acaagcactc ccac                                           24

<210> SEQ ID NO 10
<211> LENGTH: 23
<212> TYPE: DNA
<213> ORGANISM: Artificial Sequence
<220> FEATURE:
<223> OTHER INFORMATION: Reverse PCR primer for Alkaline phosphatase
      gene

<400> SEQUENCE: 10
tccgtcacgt tgttcctgtt cag                                            23

<210> SEQ ID NO 11
<211> LENGTH: 21
<212> TYPE: DNA
<213> ORGANISM: Artificial Sequence
<220> FEATURE:
<223> OTHER INFORMATION: Forward PCR primer for COL1A1 gene

<400> SEQUENCE: 11
gcggctcccc attttatac c                                               21

<210> SEQ ID NO 12
<211> LENGTH: 24
<212> TYPE: DNA
<213> ORGANISM: Artificial Sequence
<220> FEATURE:
<223> OTHER INFORMATION: Reverse PCR primer for COL1A1 gene

<400> SEQUENCE: 12
gctctcctcc catgttaaat agca                                           24

<210> SEQ ID NO 13
<211> LENGTH: 19
<212> TYPE: DNA
<213> ORGANISM: Artificial Sequence
<220> FEATURE:
<223> OTHER INFORMATION: Forward PCR primer for BMP2 gene

<400> SEQUENCE: 13
gcgtgaaaag agagactgc                                                 19

<210> SEQ ID NO 14
<211> LENGTH: 19
<212> TYPE: DNA
<213> ORGANISM: Artificial Sequence
<220> FEATURE:
<223> OTHER INFORMATION: Reverse PCR primer for BMP2 gene

<400> SEQUENCE: 14
ccattgaaag agcgtccac                                                 19

<210> SEQ ID NO 15
<211> LENGTH: 22
<212> TYPE: DNA
<213> ORGANISM: Artificial Sequence
<220> FEATURE:
<223> OTHER INFORMATION: Forward PCR primer for BMP4 gene

<400> SEQUENCE: 15
acggtgggaa acttttgatg tg                                             22
```

```
<210> SEQ ID NO 16
<211> LENGTH: 21
<212> TYPE: DNA
<213> ORGANISM: Artificial Sequence
<220> FEATURE:
<223> OTHER INFORMATION: Reverse PCR primer for BMP4 gene

<400> SEQUENCE: 16
cgagtctgat ggaggtgagt c                                            21

<210> SEQ ID NO 17
<211> LENGTH: 21
<212> TYPE: DNA
<213> ORGANISM: Artificial Sequence
<220> FEATURE:
<223> OTHER INFORMATION: Forward PCR primer for Osteoprotegerin gene

<400> SEQUENCE: 17
ggaaccccag agcgaaatac a                                            21

<210> SEQ ID NO 18
<211> LENGTH: 21
<212> TYPE: DNA
<213> ORGANISM: Artificial Sequence
<220> FEATURE:
<223> OTHER INFORMATION: Reverse PCR primer for Osteoprotegerin gene

<400> SEQUENCE: 18
cctgaagaat gcctcctcac a                                            21

<210> SEQ ID NO 19
<211> LENGTH: 18
<212> TYPE: DNA
<213> ORGANISM: Artificial Sequence
<220> FEATURE:
<223> OTHER INFORMATION: Forward PCR primer for beta actin gene

<400> SEQUENCE: 19
cattgccgac aggatgca                                                18

<210> SEQ ID NO 20
<211> LENGTH: 21
<212> TYPE: DNA
<213> ORGANISM: Artificial Sequence
<220> FEATURE:
<223> OTHER INFORMATION: Reverse PCR primer for beta actin gene

<400> SEQUENCE: 20
catctgctgg aaggtggaca g                                            21
```